United States Patent
Hsu et al.

(10) Patent No.: US 8,777,895 B2
(45) Date of Patent: Jul. 15, 2014

(54) SYSTEM AND METHOD FOR AUTHORIZED MEDICATION DELIVERY

(75) Inventors: Kenneth A. Hsu, Highland Park, IL (US); Steven R. Wehba, Carlsbad, CA (US); Todd A. Parker, Escondido, CA (US)

(73) Assignee: Hospira, Inc., Lake Forest, IL (US)

( * ) Notice: Subject to any disclaimer, the term of this patent is extended or adjusted under 35 U.S.C. 154(b) by 1021 days.

(21) Appl. No.: 12/652,140

(22) Filed: Jan. 5, 2010

(65) Prior Publication Data

US 2010/0174229 A1    Jul. 8, 2010

Related U.S. Application Data

(60) Provisional application No. 61/142,704, filed on Jan. 6, 2009.

(51) Int. Cl.
*A61M 31/00* (2006.01)
(52) U.S. Cl.
USPC .......................................................... 604/66
(58) Field of Classification Search
USPC .......................................... 604/66; 600/300
See application file for complete search history.

(56) References Cited

U.S. PATENT DOCUMENTS

| | | | |
|---|---|---|---|
| 4,551,133 A | 11/1985 | Zegers de Beyl et al. | |
| 5,713,856 A | 2/1998 | Eggers et al. | |
| 5,961,448 A | 10/1999 | Swenson et al. | |
| 6,428,483 B1 | 8/2002 | Carlebach | |
| 6,519,569 B1 | 2/2003 | White et al. | |
| 6,628,809 B1 | 9/2003 | Rowe et al. | |
| 6,731,989 B2 | 5/2004 | Engleson et al. | |
| 6,790,198 B1 | 9/2004 | White et al. | |
| 6,816,605 B2 | 11/2004 | Rowe et al. | |
| 6,899,695 B2 * | 5/2005 | Herrera | 604/65 |
| 6,948,492 B2 | 9/2005 | Wermeling et al. | |
| 6,958,691 B1 | 10/2005 | Anderson et al. | |
| 6,961,448 B2 * | 11/2005 | Nichols et al. | 382/115 |
| 6,997,880 B2 | 2/2006 | Carlebach et al. | |
| 7,193,514 B2 | 3/2007 | Ritson | |
| 7,236,936 B2 | 6/2007 | White et al. | |
| 7,263,213 B2 | 8/2007 | Rowe | |
| 7,384,410 B2 | 6/2008 | Eggers et al. | |
| 7,420,472 B2 | 9/2008 | Tran | |
| 7,489,808 B2 | 2/2009 | Gerder | |
| 7,559,321 B2 | 7/2009 | Wermeling et al. | |
| 7,572,230 B2 | 8/2009 | Neumann et al. | |
| 7,578,802 B2 | 8/2009 | Hickle | |
| 7,645,258 B2 * | 1/2010 | White et al. | 604/67 |
| 7,766,863 B2 | 8/2010 | Gillespie, Jr. et al. | |
| 7,806,852 B1 * | 10/2010 | Jurson | 604/65 |
| 7,871,394 B2 | 1/2011 | Halbert et al. | |
| 8,048,040 B2 | 11/2011 | Kiani | |
| 8,234,128 B2 | 7/2012 | Martucci et al. | |

(Continued)

FOREIGN PATENT DOCUMENTS

WO    2005050526 A2    6/2005

*Primary Examiner* — Nicholas Lucchesi
*Assistant Examiner* — Diva K Chander
(74) *Attorney, Agent, or Firm* — Michael R. Crabb

(57) ABSTRACT

A system and method for verifying identification of an authorized person by biometrics prior to a patient controlled analgesic medication delivery to the patient and for monitoring the delivery of medication to a patient is disclosed, along with a monitoring system and method for controlling medication delivery based on at least one monitored patient condition.

13 Claims, 10 Drawing Sheets

(56) References Cited

U.S. PATENT DOCUMENTS

| | | |
|---|---|---|
| 8,291,337 B2 | 10/2012 | Gannin et al. |
| 8,453,645 B2 | 6/2013 | Figueiredo et al. |
| 2003/0106553 A1 | 6/2003 | Vanderveen |
| 2003/0135087 A1 | 7/2003 | Hickle et al. |
| 2004/0039257 A1* | 2/2004 | Hickle ............ 600/300 |
| 2005/0144043 A1 | 6/2005 | Holland et al. |
| 2005/0177096 A1 | 8/2005 | Bollish et al. |
| 2005/0278194 A1 | 12/2005 | Holland et al. |
| 2007/0156282 A1* | 7/2007 | Dunn ............ 700/244 |
| 2007/0179448 A1 | 8/2007 | Lim et al. |
| 2007/0186923 A1* | 8/2007 | Poutiatine et al. ....... 128/200.14 |
| 2007/0299687 A1 | 12/2007 | Palmer et al. |
| 2013/0096444 A1 | 4/2013 | Condurso et al. |

* cited by examiner

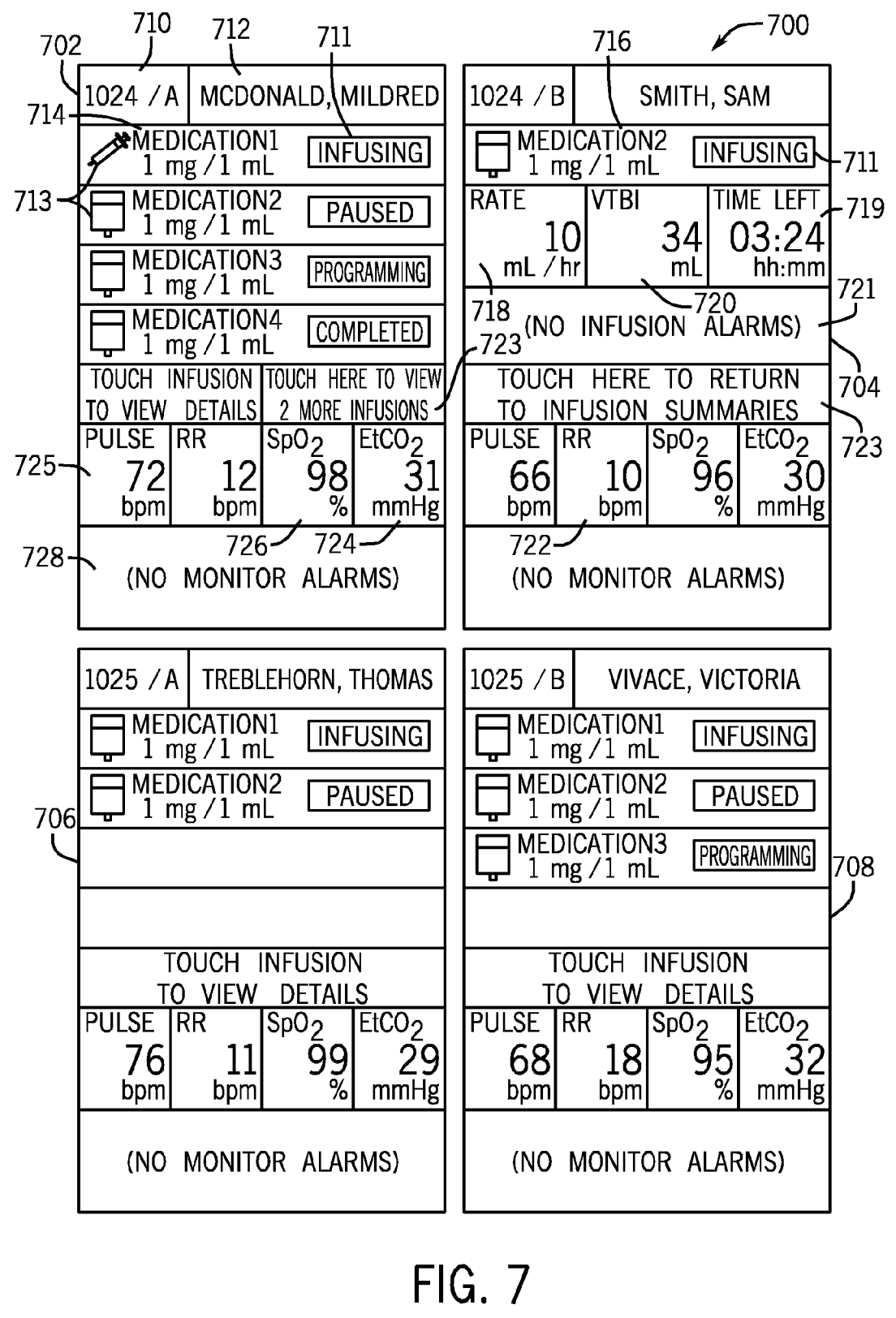

| 1024 / A | MCDONALD, MILDRED | | 1024 / B | SMITH, SAM | |
|---|---|---|---|---|---|
| MEDICATION1 1 mg / 1 mL | INFUSING | | MEDICATION2 1 mg / 1 mL | INFUSING | |
| MEDICATION2 1 mg / 1 mL | PAUSED | | RATE 10 mL / hr | VTBI 34 mL | TIME LEFT 03:24 hh:mm |
| MEDICATION3 1 mg / 1 mL | PROGRAMMING | | (NO INFUSION ALARMS) | | |
| MEDICATION4 1 mg / 1 mL | COMPLETED | | | | |
| TOUCH INFUSION TO VIEW DETAILS | TOUCH HERE TO VIEW 2 MORE INFUSIONS | | TOUCH HERE TO RETURN TO INFUSION SUMMARIES | | |
| PULSE 72 bpm | RR 12 bpm | SpO$_2$ 98 % | EtCO$_2$ 31 mmHg | | |
| PULSE 66 bpm | RR 10 bpm | SpO$_2$ 96 % | EtCO$_2$ 30 mmHg | | |
| (NO MONITOR ALARMS) | | | (NO MONITOR ALARMS) | | |

| 1025 / A | TREBLEHORN, THOMAS | | 1025 / B | VIVACE, VICTORIA | |
|---|---|---|---|---|---|
| MEDICATION1 1 mg / 1 mL | INFUSING | | MEDICATION1 1 mg / 1 mL | INFUSING | |
| MEDICATION2 1 mg / 1 mL | PAUSED | | MEDICATION2 1 mg / 1 mL | PAUSED | |
| | | | MEDICATION3 1 mg / 1 mL | PROGRAMMING | |
| TOUCH INFUSION TO VIEW DETAILS | | | TOUCH INFUSION TO VIEW DETAILS | | |
| PULSE 76 bpm | RR 11 bpm | SpO$_2$ 99 % | EtCO$_2$ 29 mmHg | | |
| PULSE 68 bpm | RR 18 bpm | SpO$_2$ 95 % | EtCO$_2$ 32 mmHg | | |
| (NO MONITOR ALARMS) | | | (NO MONITOR ALARMS) | | |

FIG. 7

SYSTEM AND METHOD FOR AUTHORIZED MEDICATION DELIVERY

CROSS-REFERENCE TO RELATED APPLICATIONS

This application claims priority based upon U.S. Provisional Patent Application Ser. No. 61/142,704 filed on Jan. 6, 2009.

FEDERALLY SPONSORED RESEARCH OR DEVELOPMENT

None.

TECHNICAL FIELD

The present invention relates to systems and methods for delivering medication, such as an analgesic, to a patient, for example, utilizing a patient controlled analgesia (PCA) request device in communication with a medication delivery device, such as an infusion pump. The present invention is also directed to systems and methods for monitoring patient conditions. More particularly, the present invention relates to a system and method for preventing delivery of a medication, such as by assistive or proxy delivery of an analgesic agent using a PCA request device in communication with a medication delivery device, without proper authentication that the person requesting the medication is the patient or an authorized person.

BACKGROUND OF THE INVENTION

Modern medical care often involves the use of medication management systems, which include medication delivery and monitoring devices such as medication delivery pumps and/or patient condition monitors. Medication management systems for configuring, controlling, and monitoring medication delivery devices have been disclosed. For example, commonly owned U.S. patent application Ser. No. 10/930,358, which published as US20050144043A1 on Jun. 30, 2005 and U.S. patent application Ser. No. 10/783,573, which published as US20050278194A1 on Dec. 15, 2005, disclose a medication management system in which customizable drug library or medical device configuration information is prepared using a drug library editor (DLE) program and module of a medication management unit (MMU). The MMU downloads the customizable drug library to the medication delivery pump and receives status or activity information from the pump. Commonly owned U.S. patent application Ser. No. 10/783,877, which also published as WO2005050526A2 on Jun. 2, 2005, discloses how the drug library or medical device configuration information is created, edited, stored and communicated to a medication delivery device in the context of a medication management system to deliver substances, such as fluids and/or fluid medication to patients. According to the above-mentioned commonly owned published patent applications, a typical medication management system includes a point of care computer, such as a barcode point of care computer and/or pharmacy computer, and/or an MMU, in communication with one or more medication delivery devices. The point of care computer(s) and/or the MMU, with associated memory, store various information, such as patient information, prescription information, customized drug library or other information, for managing medication delivery to a patients, such as performing five-rights checking, configuring the medication delivery devices, and receiving and storing activity information received from the medication delivery devices.

As mentioned, the medication delivery devices can include electronic medical pumps. The medical pumps can be used with PCA (patient controlled analgesia) request devices in which a patient can "self-deliver" medication, such as an analgesia or analgesic. For example, U.S. Pat. No. 4,551,133, to Zeggers de Beyl et al., issued Nov. 5, 1985, discloses a patient controlled analgesia system for introducing medication to a peripheral vein of a patient. The patient can request the administration of an analgesic or analgesia by using a PCA request device. The delivery of the analgesic is controlled by a microprocessor based system in response to the patient's physiological conditions. Specifically, the microprocessor is associated with a remote patient control or PCA request device, for providing an actuation signal to the microprocessor when the patient requests a delivery of medication. Modern PCA pumps can also be programmed by caregivers to limit the response of the pump to a delivery request in terms of bolus amount or volume allowed, duration, frequency or lockout interval between boluses, and hourly limit.

Quite often, PCA pumps are used in post-operative settings after a patient has become conscious but is or would be in significant pain without the delivery of the analgesic. In addition, quite often, these patients are no longer held in a separate post-operative recovery area with limited visitation privileges. Instead, such patients are often placed within standard patient rooms and allowed regular visitation by friends and relatives. Some patients even use PCA pumps for pain management at their homes or in a hospice setting. Therefore, in many cases, patients, as well as their friends and relatives, are not directly supervised when the patient requests delivery of medication, such as an analgesic, using the PCA request device. In such setting, an overzealous relative or friend may attempt to utilize the PCA request device on behalf of or as a proxy for the patient, such as for example when the patient is sleeping or unconscious. While perhaps well intentioned, these actions can lead to significant injury to the patient.

Thus, one objective of the present invention is the provision of at least a method and system for patient controlled analgesic medication delivery to the patient and for monitoring the delivery of medication to a patient.

All of the patents and patent application referred to within this Background of the Invention section of the present specification are hereby incorporated by reference and made a part of this specification. In addition, the present invention is provided to solve the problems discussed above and, to provide advantages and aspects not provided by prior medical systems, as well as achieve other objects not explicitly stated above. A full discussion of the features, advantages and objects of the present invention is deferred to the following detailed description, which proceeds with reference to the accompanying drawings.

SUMMARY OF THE INVENTION

The invention relates to systems and methods for verifying identification of an authorized person prior to a patient controlled analgesic medication delivery to the patient and for monitoring the delivery of medication to a patient. Thus, in one embodiment, the present invention is directed to a system and method for verifying identification of an authorized person prior to a patient controlled analgesic medication delivery to the patient. The system and method receives a medication request signal from a patient controlled analgesia (PCA) request device in communication with a processor, representing that the PCA request device has been actuated. From a biometric receiver in communication with the processor, the system and method further receives a biometric identification signal representing a biometric identifier of a person. The system and method retrieves from a memory in communication with the processor at least one stored biometric identifier representing at least one person that is authorized to actuate the PCA request device for the patient, and determines whether the received biometric identifier matches the at least one stored biometric identifier.

In one embodiment, if the received biometric identifier does not match the at least one stored biometric identifier, the system and method prevents delivery of the patient controlled analgesic medication delivery to the patient, and transmits an alarm signal for alarming an audible alarm device. If the received biometric identifier matches the at least one stored biometric identifier, the system and method transmits a delivery signal for patient controlled analgesic medication delivery.

In another embodiment, when the system and method receives the medication request signal from the patient controlled analgesia (PCA) request device, the processor is triggered to transmit a biometric scan request signal, and thereafter receives the biometric identification signal from the biometric receiver.

In another embodiment, the at least one stored biometric identifier is stored in a memory located remotely from the PCA request device and biometric receiver, and the at least one stored biometric identifier is retrieved from the remote memory which is in communication with the processor. The processor can also receive the at least one stored biometric identifier from the remote memory, and determine whether the received biometric identifier matches the at least one stored biometric identifier.

In a further embodiment, the system and method can also transmit the received biometric identifier to a remote computer. The system and method receives at the remote computer the at least one stored biometric identifier from the remote memory, and determines at the remote computer whether the received biometric identifier matches the at least one stored biometric identifier, thereby generating a match result. If the match result represents that received biometric identifier does not match the at least one stored biometric identifier, the system and method transmits a match result signal to the processor, representing the match result, and prevents delivery of the PCA medication delivery to the patient.

In another embodiment, the system and method receives an initial biometric signal from the biometric receiver, representing an initial biometric identifier of a person. The system and method also receives associated identification information for the person, and associates the associated identification information with the initial biometric identifier and with patient information, for designating the person as authorized to actuate the PCA request device for the patient. In addition, the system and method stores the initial biometric identifier to create the stored biometric identifier, and stores the associated identification information in the memory.

In a further embodiment, the biometric receiver which transmits the initial biometric signal is a first biometric receiver, and the biometric receiver that transmits the biometric identification signal is a second biometric receiver. In another embodiment, the first biometric receiver is located remotely from the PCA request device and the second biometric receiver.

In another embodiment, the system and method is directed to verifying identification of an authorized person prior to a patient controlled analgesic medication delivery to the patient. The system and method receive a biometric identification signal from the biometric receiver that is in communication with the processor, representing a biometric identifier of a person. The system and method then retrieves at least one stored biometric identifier from a memory in communication with the processor, representing at least one person that is authorized to actuate the a patient controlled analgesia (PCA) request device in communication with the processor, and determines whether the received biometric identifier matches the at least one stored biometric identifier. If the received biometric identifier matches the at least one stored biometric identifier, the system and method enable the PCA request device for a predetermined limited period of time, which then allows the system and method to receive a medication request signal from the PCA request device, representing that the PCA request device has been actuated. If the medication request signal is received from the PCA request device within the predetermined period limited period of time, the system and method then transmits a delivery signal for patient controlled analgesic medication delivery.

In another embodiment, the system and method is directed to monitoring patient conditions during the delivery of medication to a patient. The system and method receive patient condition signals at a patient condition monitor for monitoring at least one condition of the patient. The system and method further receive the patient condition information at a medical pump or a central computer from the patient condition monitor. The patient condition information represents at least one condition of the patient. Medication delivery status information is tracked and stored at the medical pump as well. The medication delivery status information represents the past and present status of a medication delivery provided by the medical pump to a patient. The patient condition information and the medication delivery status information is transmitted to and received at the central computer. The patient condition information and medication delivery/medical pump status information is transmitted from the central computer to the caregiving computer and displayed at the caregiving computer.

In the process of establishing a monitoring session for monitoring the patient condition information or monitoring the medical pump status information, the system and method can read a medication container barcode comprising a medication ID of a medication, a patient barcode comprising a patient ID, a patient room barcode comprising a patient room ID, and/or a medical pump barcode comprising a medical pump ID, with a barcode reader in communication with the medical pump. The barcode reader can be integral with, tethered to, or separate from the medical pump. The system and method can transmit the medication ID, patient ID, patient room ID, and/or medical pump ID from the medical pump to the central computer for use at least by the central computer in establishing a monitoring session. Alternatively, or in addition, the patient condition information and the medical pump status information received by the central computer can be transmitted to a PDA (personal digital assistant) carried and used by a caregiver. The patient condition information and medical pump status information is received by and displayed at the PDA for viewing by the caregiver.

In another embodiment, a respiratory condition signal representing a respiratory level of the patient is received by the patient condition monitor and is transmitted to central computer or to the medical pump, which in turns transmits the respiratory signal to a central computer. The monitor, central computer or the pump determines whether the respiratory level of the patient satisfies at least one predetermined respiratory parameter. If respiratory level of the patient satisfies the predetermined respiratory parameter, the monitor, central computer or pump can be configured to transmit a respiratory distress signal or alarm to at least one of the caregiving computer and/or a PDA, and also transmit a pause signal to the medical pump to pause the medication delivery, among other tasks.

Other features and advantages of the invention will be apparent from the following specification taken in conjunction with the following drawings.

BRIEF DESCRIPTION OF THE DRAWINGS

To understand the present invention, it will now be described by way of example, with reference to the accompanying drawings.

FIG. 7 is one embodiment of an interface screen display showing at least a subset of patient condition information and medical pump status information.

DETAILED DESCRIPTION

Figure 1:
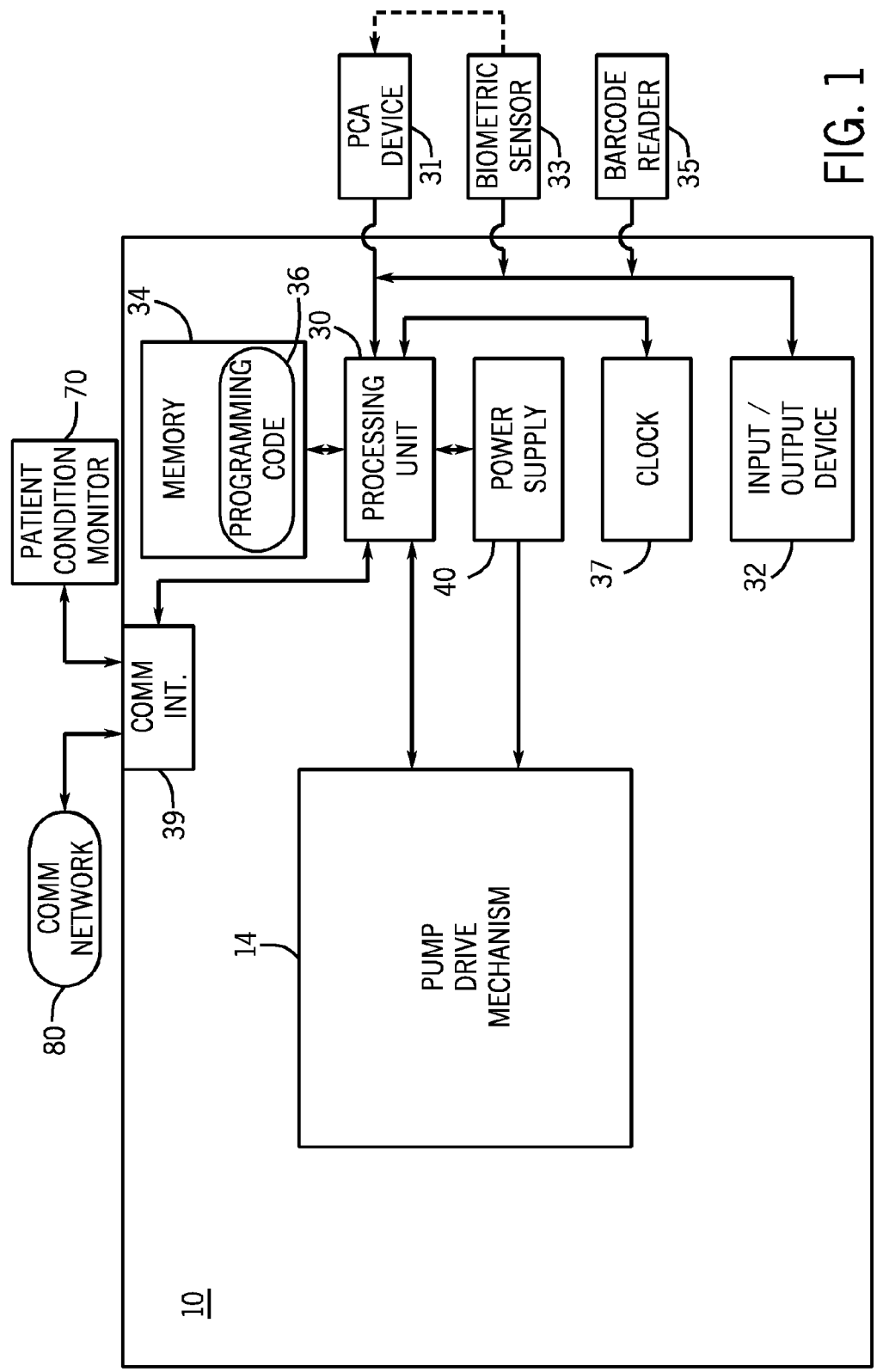
FIG. 1 is a diagram of one embodiment of a medication delivery device within the system and method for delivering medication according to the present invention.

While this invention is susceptible of embodiments in many different forms, there is shown in the drawings and will herein be described in detail preferred embodiments of the invention with the understanding that the present disclosure is to be considered as an exemplification of the principles of the invention and is not intended to limit the broad aspect of the invention to the embodiments illustrated. A medication delivery pump or medical pump includes but is not limited to enteral pumps, infusion pumps, cassette pumps, syringe pumps, peristaltic pumps, or any positive displacement fluid pumping device for the delivery of fluids intravenously or intra-arterially to a patient. Referring initially to FIG. 1, one embodiment of a medical pump 10 is provided and can be used for delivering a substance, such as a fluid, to a patient. In one embodiment of the medical pump, the medical pump is a LIFECARE PCA pump, which is available from Hospira, Inc. of Lake Forest, Ill., U.S.A., but the invention is applicable to other types of medical pumps. The medical pump 10 has a pump drive mechanism 14 for delivering the substance or medication. A processing unit or processor 30 is included in pump 10. The processor 30 is configured to control the pump drive mechanism 14 and performs various operations, as described in greater detail herein. An input/output device 32 communicates with the processing unit 30 and allows the user to receive output from processing unit 30 and/or input information or commands into the processing unit 30. Those of ordinary skill in the art will appreciate that input/output device 32 may be provided as a separate display device and/or a separate input device. For example, in one embodiment of the present invention, the medical pump 10 includes a patient-controlled analgesia (PCA) request device 31 which is in communication with the processor 30, for receiving an input from a person to generate a medication request signal from the PCA request device 31, for transmission to and receipt by the processor 30, as described in greater detail herein. The request signal represents that the PCA request device 31 has been actuated, such as by the patient, a caregiver, or by another person in the vicinity of the PCA request device. As another example, the medical pump 10 can also include a biometric receiver, reader or scanner 33, in communication with the processor 30, for receiving an input from a person to generate a biometric identification signal, for transmission to and receipt by the processor 30, as described in greater detail herein. As illustrated in FIG. 1, the biometric receiver or scanner 33 can communicate directly with the processor 30, indirectly through the PCA request device 31, or even be integrated into the PCA request device 31. The biometric identification signal represents a biometric identifier of a person, such as the patient, the caregiver, or another person, for at least determining whether the person is authorized to deliver medication to the patient. The biometric receiver 33 can be a fingerprint reader, a hand reader, an iris scanner, a face scanner, a DNA reader, a voice recognition reader, a keyboard keystroke pattern recognition device, a signature recognition device, or other receiver that can scan or read a physiological or behavioral characteristic of a person that is unique or at least semi-unique to that person, and which can be used to identify that person. The biometric receiver 33 can be integral with the medical pump 10 or can be a separate device which is in communication with or connected to the medical pump 10 through a wired connector or other wired or wireless interface device.

As a further example, the medical pump 10 can also include a code or identification reader or receiver 35, such as a bar code reader, RFID tag reader, or other code reader, in wired or wireless communication with the processor 30, for reading an/or scanning a code or ID and transmitting the code or ID to the processor 30. The code or ID can represent an identification, or pointer to a location in a memory which stores the identification, of a medication, a patient, a caregiver, the medical pump, and/or other identification used within a medication delivery system, such as the medication delivery systems described in one or more of the patents and/or patent applications referred to within the Background of the Invention section herein.

A memory 34 communicates with the processor 30 and stores code and data necessary for the processor 30 to calculate and output the operating conditions of the pump 10. The memory 34 stores a programming code 36, such as a medication delivery programming code or application, formed in accordance with the present invention for processing data to determine and control the operating condition of the medical pump 10. A clock 37 is used to keep time in the pump 10. The clock 37 is connected to the processor 30, and provides the processor 30 with time information for correlating data over time or conducting time sensitive activities. The pump drive mechanism 14 is controlled by processor 30 and is energized by a battery or AC power supply 40.

With continued reference to FIG. 1, the medical pump 10 can also include a communications interface 39, in communication with the processor 30, for transmitting/receiving communications between the processor 30 and local medical devices that can be connected therewith in a wired or wireless manner, such as a patient condition monitor 70, as described in greater detail herein. Additionally or alternatively, the communications interface 39 can be provided for transmitting/receiving communications between the processor 30 and a communications network 80, including between the processor 30 and other devices that are linked or in communication with the communications network 80. For example, referring to FIGS. 2 and 3, two embodiments of a medication management and/or patient condition monitoring system 200, 300 are shown, each having a central computer 202, 302. The central computer 202, 302 in each system 200, 300 can have a central processor and a central memory associated therewith. Each central memory can include a central programming code, such as a central medication management application 202, 302 and/or central patient monitoring application 202, 302, and other applications, for execution by the central processor, which can perform various medication management, patient monitoring, and other functions, as described in greater detail herein. Each medication management system 200, 300 can also include one or more medication delivery pumps 210, 310, such as the medical pump 10 shown in FIG. 1. Communications can be transmitted/received between the processor 30/the medication delivery pump 10, 210, 310 and the central computer 202, 302, as well as the central programming code executing therein, through the communications network 80, 280, 380 and the communications interface 39, as described in greater detail herein. Similar to the medical pump 10 of FIG. 1, the medical pumps 210, 310 of FIGS. 2 and 3 also include a processor and a medication delivery application 210, 310, among other elements and functions of the medical pump 10 of FIG. 1, as described in greater detail herein. Further, the medical pump 10, 210, 310 can include many aspects of a LIFECARE PCA® Infusion System, and the medication management application 202, 302 within the central computer 202, 302, can include many aspects of HOSPIRA MEDNET® (Java-based) Software, both manufactured and sold by Hospira, Inc., the assignee of the present invention, in conjunction with the present invention.

Figure 2:
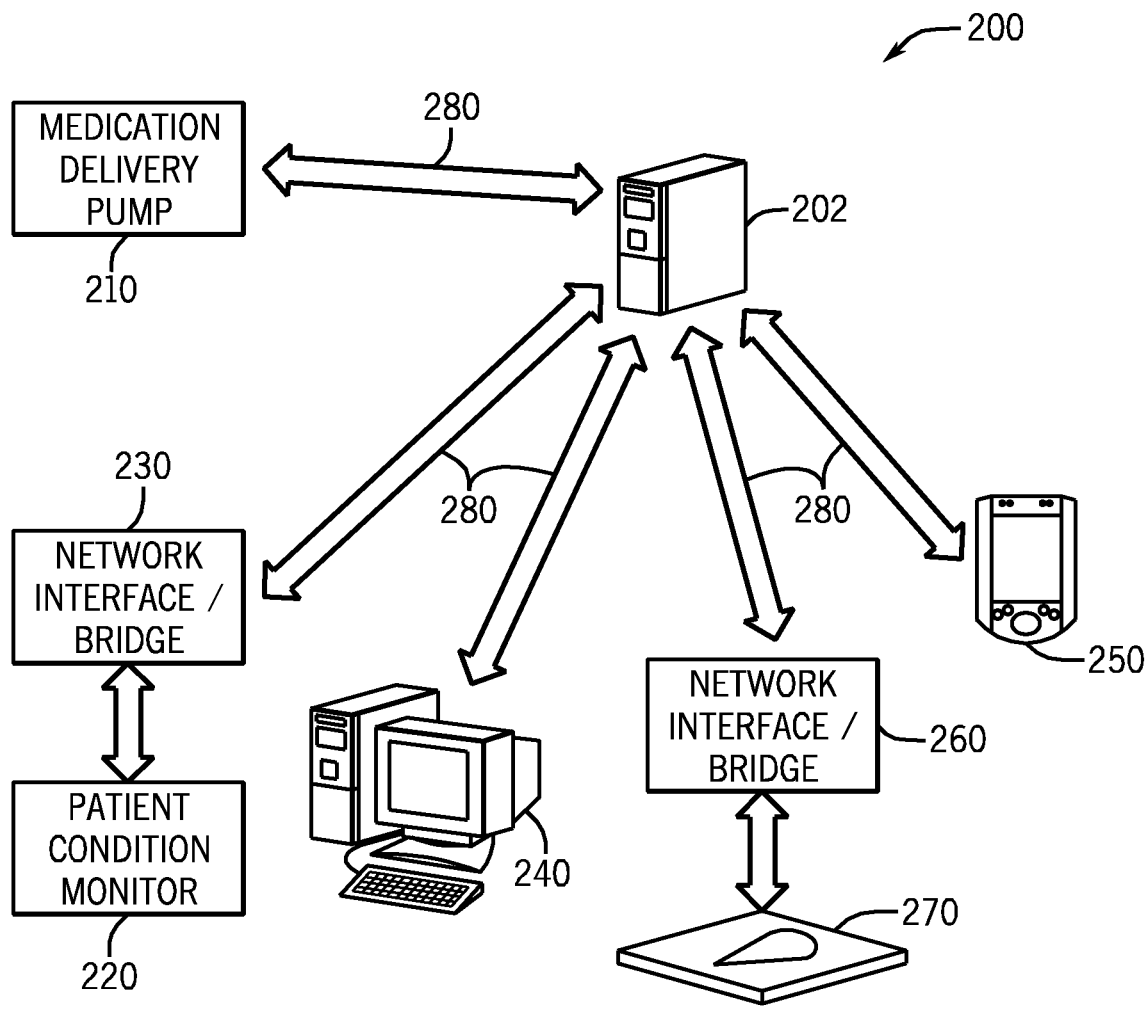
FIG. 2 is a system diagram of one embodiment of the system and method for delivering medication and/or for patient condition monitoring according to the present invention.

With continued reference to FIG. 2, the medication management system 200 also includes a patient condition monitor 220 in communication with a network interface/bridge 230. The patient condition monitor 220 can be any monitor that senses, measures, or analyzes one or more physiological condition of the patient, including but not limited to EEGs, ECGs, monitors for temperature, blood pressure, SpO2, CO2, SaO2, heart or pulse rate, cardiac output, respiration rate, blood glucose, blood gases or electrolytes, etc. The network interface 230 can include a processor and network interface application for providing network interfacing functionality. Specifically, the network interface 230 is in communication with the communications network 280, for allowing communications to be transmitted/received between the patient condition monitor 220 and the central computer 202, and medication management application 202 therein, as described in greater detail herein. With additional reference to FIG. 3, preferably, the medication management system 300 also includes a patient condition monitor 320 in communication with the medication delivery pump 310. The communication can be wireless, or for greater security and to avoid the potential for loss of wireless signal a cable may connect the patient condition monitor 320 with the medication delivery pump 310. The patient condition monitor 220, 320 in FIGS. 2 and 3 can include a processor and patient monitoring application for monitoring conditions of the patient to which the patient condition monitor 220, 320 is attached, for transmitting the monitored conditions of the patient to other devices and/or the central computer 202, 302. The monitored conditions can include the patient's physiological conditions and alarms or alerts related to those conditions. For example, in FIG. 3, the medication delivery pump 310 is in communication with the communications network 380, for at least allowing communications to be transmitted/received between the patient condition monitor 320 and the central computer 302, and medication management application 302 therein, for transmission of the patient conditions to the medical pump 310 and to the central computer 302, as described in greater detail herein.

Figure 3:
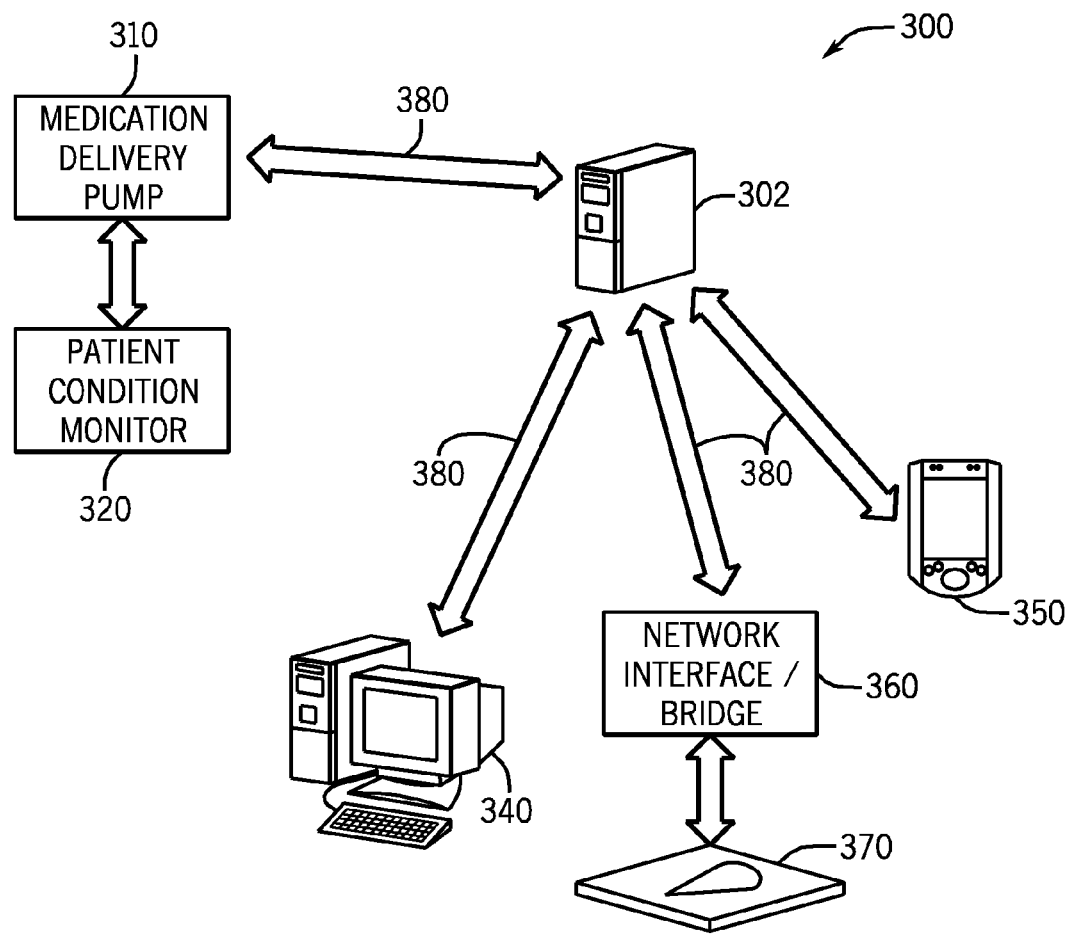
FIG. 3 is a system diagram of an alternative embodiment of the system and method for delivering medication and/or for patient condition monitoring of FIG. 2.

The medication management systems 200, 300 shown in FIGS. 2 and 3 can each further include a caregiver computer 240, 340 in communication with the central computer 202, 302, and medication management application 202, 302 therein, for at least allowing communications to be transmitted/received between the caregiver computer 240, 340 and the central computer 202, 302 over a communications network 280, 380 as described in greater detail herein. In one embodiment, the caregiver computer 240, 340 can be in the patient's room. In another embodiment the caregiver computer 240, 340 can be located in a caregiver or nurses station, and include a plurality of caregiver computers and/or computer monitors, for monitoring one or more patients and the biological and/or medical condition of the one or more patients. Each central computer 202, 302 and/or caregiver computer 240, 340 can include a patient monitoring/nurses' station application, as a part of or separate from the medication management application, for performing patient monitoring functions, as described in greater detail herein. The caregiver computer 240 can include a processor and memory for executing and storing the patient monitoring/nurses' station application. The medication management systems 200, 300 shown in FIGS. 2 and 3 each also include one or more personal digital assistant computer (PDA) 250, 350, such as a pager, cell phone or other PDA, in communication with the central computer 202, 302, and medication management application 202, 302 therein, for at least allowing communications to be transmitted/received between the PDA 250 and the central computer 202, 302 over a communications network 280, as described in greater detail herein. The PDAs 250, 350 can be used by the caregivers to carry with them as the caregivers perform caregiving functions, such as performing scheduled rounds in which the caregivers deliver medication to patients in patient rooms within a caregiving facility. In such an arrangement, the caregiver will be away from the caregiver computer(s) 240, 340, and may need another mechanism to appropriately monitor patient conditions, for at least patients to which such caregiver is assigned. In one embodiment, the PDAs 250, 350 can monitor one or more patients and the biological and/or medical condition of the one or more patients. Each central computer 202, 302 and/or caregiver computer 240, 340 and/or PDA 250, 350 can include a patient monitoring application, as a part of or separate from the medication management application, for performing these monitoring functions, as described in greater detail herein. The PDA 250, 350 can include a processor and memory for executing and storing the PDA patient monitoring application.

As shown in FIGS. 2 and 3, each medication management system 200, 300 can also include a system biometric receiver

270, 370 in communication with a further network interface/ bridge 260, 360, for receiving an input from a person to generate an initial biometric identification signal, for transmission to and receipt by a processor, such as the central computer 202, 302, as described in greater detail herein. The network interface 260, 360 can include a processor, a memory and network interface application, executing on the processor and stored within the memory, for providing network interfacing functionality. The biometric identification signal represents a biometric identifier of a person, such as the patient, the caregiver, or another person, for at least receiving and storing an initial biometric identifier of a person as well as associated identification information for the person. The system biometric receiver 270, 370 can be a fingerprint reader, a hand reader, an iris scanner, a face scanner, a DNA reader, a voice recognition reader, a keyboard keystroke pattern recognition device; a signature recognition device, or other receiver that can scan or read a physiological or behavioral characteristic of a person that is unique or at least semi-unique to that person, and which can be used to identify that person. The system biometric receiver 270, 370 and/or the central computer 202, 302 can include an appropriate biometric application for performing biometric identification functions, as described in greater detail herein. In one embodiment, the system biometric receiver can have a processor and memory to execute and store the biometric application. Further, in one embodiment, the system biometric receiver 270, 370 is in addition to the biometric receiver 33 that can be a part of or in communication with the medical pump 10, 210, 310. Each network interface 260, 360 is in communication with the communications network 280, 380, for allowing communications to be transmitted/received between the system biometric receiver 270, 370 and the central computer 202, 302, and medication management application 202, 302 therein, as described in greater detail herein. Referring to FIGS. 2 and 3, the central computer 202, 302 or central care system and central medication management application and/or central patient monitoring application therein, can take the form of a pharmacy information computer or system (PhIS), a hospital information system (HIS), and/or a central point of care (POC) system), and/or can be separate therefrom. The medication management and/or patient condition monitoring system 200, 300 for delivering medication and for monitoring patient conditions, and the methods and applications therein, can be implemented in software, firmware, hardware, or a combination thereof. In one mode, the medication management and/or patient condition monitoring system 200, 300 and methods are implemented in software, as one or more executable programs or applications, and is executed by one or more special or general purpose digital computer(s), such as a personal computer (PC; IBM-compatible, APPLE-compatible, or otherwise), personal digital assistant, workstation, minicomputer, server, and/or mainframe computer. Therefore, the medical pumps 210, 310, network interfaces 230, 330, 260, 360, patient condition monitors 220, 320, central computers 202, 302, caregiver computers 240, 340, biometric receivers 270, 370, and PDA computers 250, 350 may be representative of any computers in which the applications of the medication management and/or patient condition monitoring systems 200, 300 reside or partially reside.

Generally, in terms of hardware architecture, as shown in FIGS. 1, 2 and 3 the medical pumps 10, 210, 310, network interfaces 39, 230, 330, 260, 360, patient condition monitors 70, 220, 320, central computers 202, 302, caregiver computers 240, 340, biometric receivers 33, 270, 370, and PDA computers 250, 350 of the medication management and/or patient condition monitoring systems 200, 300, include a processor, memory, and one or more input and/or output (I/O) devices (or peripherals) that are communicatively coupled via a local interface. The local interface can be, for example, but not limited to, one or more buses or other wired or wireless connections, as is known in the art. The local interface may have additional elements, such as controllers, buffers (caches), drivers, repeaters, and receivers, to enable communications. Further, the local interface may include address, control, and/or data connections to enable appropriate communications among the other computer components.

The processors are hardware devices for executing software, particularly software stored in memory. The processors can be any custom made or commercially available processor, a central processing unit (CPU), an auxiliary processor among several processors associated with the medical pumps, network interfaces, patient condition monitors, central computers, caregiver computers, biometric receivers, and PDA computers of the medication management and/or patient condition monitoring systems 200, 300, a semiconductor based microprocessor (in the form of a microchip or chip set), a macroprocessor, or generally any device for executing software instructions. Examples of suitable commercially available microprocessors are as follows: a PA-RISC series microprocessor from Hewlett-Packard Company, an 80×86 or Pentium series microprocessor from Intel Corporation, a PowerPC microprocessor from IBM, a Sparc microprocessor from Sun Microsystems, Inc., or a 68xxx series microprocessor from Motorola Corporation. The processors may also represent a distributed processing architecture such as, but not limited to, EJB, CORBA, and DCOM. In one embodiment, the central computer 202, 302 is a WINDOWS based server or series of servers and the caregiver computer 240, 340 and PDA computer are each a WINDOWS based client computer.

Each memory of each the medical pumps, network interfaces, patient condition monitors, central computers, caregiver computers, biometric receivers, and PDA computers of the medication management and/or patient condition monitoring systems 200, 300, can include any one or a combination of volatile memory elements (e.g., random access memory (RAM, such as DRAM, SRAM, SDRAM, etc.)) and nonvolatile memory elements (e.g., ROM, hard drive, tape, CDROM, etc.). Moreover, these memories may incorporate electronic, magnetic, optical, and/or other types of storage media. The memories can have a distributed architecture where various components are situated remote from one another, but are still accessed by the processors of the medical pumps, network interfaces, patient condition monitors, central computers, caregiver computers, biometric receivers, and PDA computers of the medication management and/or patient condition monitoring systems 200, 300.

The software within one or more of the above referenced memories may include one or more separate programs. The separate programs comprise ordered listings of executable instructions for implementing logical functions. In the examples of FIGS. 1, 2 and 3, the software in the memories can include suitable operating systems (O/S). A non-exhaustive list of examples of suitable commercially available operating systems for at least some of these devices is as follows: (a) a WINDOWS operating system available from Microsoft Corporation; (b) a NETWARE operating system available from Novell, Inc.; (c) a MACINTOSH operating system available from Apple Computer, Inc.; (d) a UNIX operating system, which is available for purchase from many vendors, such as the Hewlett-Packard Company, Sun Microsystems, Inc., and AT&T Corporation; (e) a LINUX operating system, which is freeware that is readily available on the Internet; (f)

a run time VXWORKS operating system from WindRiver Systems, Inc.; or (g) an appliance-based operating system, such as that implemented in handheld computers or personal digital assistants (PDAs) (e.g., PalmOS™ available from Palm Computing, Inc., and WINDOWS CE available from Microsoft Corporation). The operating systems essentially control the execution of other computer programs, such as the medication delivery applications, network interface applications, patient monitoring applications, central medication management applications, central patient monitoring applications, and/or biometric applications, in accordance with the present invention, and provide scheduling, input-output control, file and data management, memory management, and communication control and related services.

The medication delivery applications, network interface applications, patient monitoring applications, central medication management applications, central patient monitoring applications, and/or biometric applications, and other source programs within the medication management and/or patient condition monitoring systems 200, 300 may be a source program, executable program (object code), script, or any other entity comprising a set of instructions to be performed. When the program is a source program, the program needs to be translated via a compiler, assembler, interpreter, or the like, which may or may not be included within the memories, so as to operate properly in connection with the O/S. Furthermore, these applications can be written as (a) an object oriented programming language, which has classes of data and methods, or (b) a procedural programming language, which has routines, subroutines, and/or functions, for example but not limited to, VB.Net, C#, C, C++, Pascal, Basic, Fortran, Cobol, Perl, Java, and Ada. Java, C++, C# and Visual Basic are the most contemporary languages. For example, in one embodiment, the embedded applications such as the medication delivery application and the biometrics application are written in C++, and the other non-embedded applications are written in Java, Visual Basic or C#.

The I/O devices referred to above may include input devices, for example input modules for PLCs, a keyboard, mouse, scanner, microphone, touch screens, interfaces for various medical devices, bar code readers, biometric receivers, PCA request devices, stylus, laser readers, radio-frequency device readers, etc. Furthermore, the I/O devices may also include output devices, for example but not limited to, output modules for PLCs, a printer, bar code printers, displays, etc. Finally, the I/O devices may further include devices that communicate both inputs and outputs, for instance but not limited to, a modulator/demodulator (modem; for accessing another device, system, or network), a radio frequency (RF) or other transceiver, a telephonic interface, a bridge, and a router.

If the medical pumps, network interfaces, patient condition monitors, central computers, caregiver computers, biometric receivers, and PDA computers of the medication management and/or patient condition monitoring systems 200, 300, are a PC, workstation, PDA, or the like, the software in the respective memories may further include a basic input output system (BIOS) (not shown in FIGS. 1, 2 and 3). The BIOS is a set of essential software routines that initialize and test hardware at startup, start the O/S, and support the transfer of data among the hardware devices. The BIOS is stored in ROM so that the BIOS can be executed when the medical pumps, network interfaces, patient condition monitors, central computers, caregiver computers, biometric receivers, and PDA computers of the medication management and/or patient condition monitoring systems 200, 300 are activated.

When the medical pumps, network interfaces, patient condition monitors, central computers, caregiver computers, biometric receivers, and PDA computers of the medication management and/or patient condition monitoring systems 200, 300, are in operation, the processors therein are configured to execute software stored within respective memories, to communicate data to and from memories, and to generally control operations of the medical pumps, network interfaces, patient condition monitors, central computers, caregiver computers, biometric receivers, and PDA computers of the medication management and/or patient condition monitoring systems 200, 300, pursuant to the software. The medication delivery applications, network interface applications, patient monitoring applications, central medication management applications, central patient monitoring applications, and/or biometric applications, and the O/S, in whole or in part, but typically the latter, are read by respective processors, perhaps buffered within the processors, and then executed.

When the medication management and/or patient condition monitoring systems 200, 300 are implemented in software, as is shown in FIGS. 1, 2, and 3, it should be noted that the application programs therein can be stored on any computer readable medium for use by or in connection with any computer related system or method. In the context of this document, a computer readable medium is an electronic, magnetic, optical, or other physical device or means that can contain or store a computer program for use by or in connection with a computer related system or method. Several of the application programs, such as the medication delivery applications, network interface applications, patient monitoring applications, central medication management applications, central patient monitoring applications, and/or biometric applications, and other source programs within the medication management and/or patient condition monitoring systems 200, 300 can be embodied in any computer-readable medium for use by or in connection with an instruction execution system, apparatus, or device, such as a computer-based system, processor-containing system, or other system that can fetch the instructions from the instruction execution system, apparatus, or device and execute the instructions. In the context of this document, a "computer-readable medium" can be any means that can store, communicate, propagate, or transport the program for use by or in connection with the instruction execution system, apparatus, or device. The computer readable medium can be for example, but not limited to, an electronic, magnetic, optical, electromagnetic, infrared, or semiconductor system, apparatus, device, or propagation medium. More specific examples (a non-exhaustive list) of the computer-readable medium would include the following: an electrical connection (electronic) having one or more wires, a portable computer diskette (magnetic), a random access memory (RAM) (electronic), a read-only memory (ROM) (electronic), an erasable programmable read-only memory (EPROM, EEPROM, or Flash memory) (electronic), an optical fiber (optical), and a portable compact disc read-only memory (CDROM) (optical). Note that the computer-readable medium could even be paper or another suitable medium upon which the program is printed, as the program can be electronically captured, via, for instance, optical scanning of the paper or other medium, then compiled, interpreted or otherwise processed in a suitable manner if necessary, and then stored in a computer memory.

In another embodiment, the medication management and/or patient condition monitoring systems 200, 300 are implemented in hardware. These systems and methods can be implemented with any, or a combination of, the following technologies, which are each well known in the art: a discrete logic circuit(s) having logic gates for implementing logic functions upon data signals, an application specific integrated circuit (ASIC) having appropriate combinational logic gates, a programmable gate array(s) (PGA), a field programmable gate array (FPGA), etc.

Figure 4:
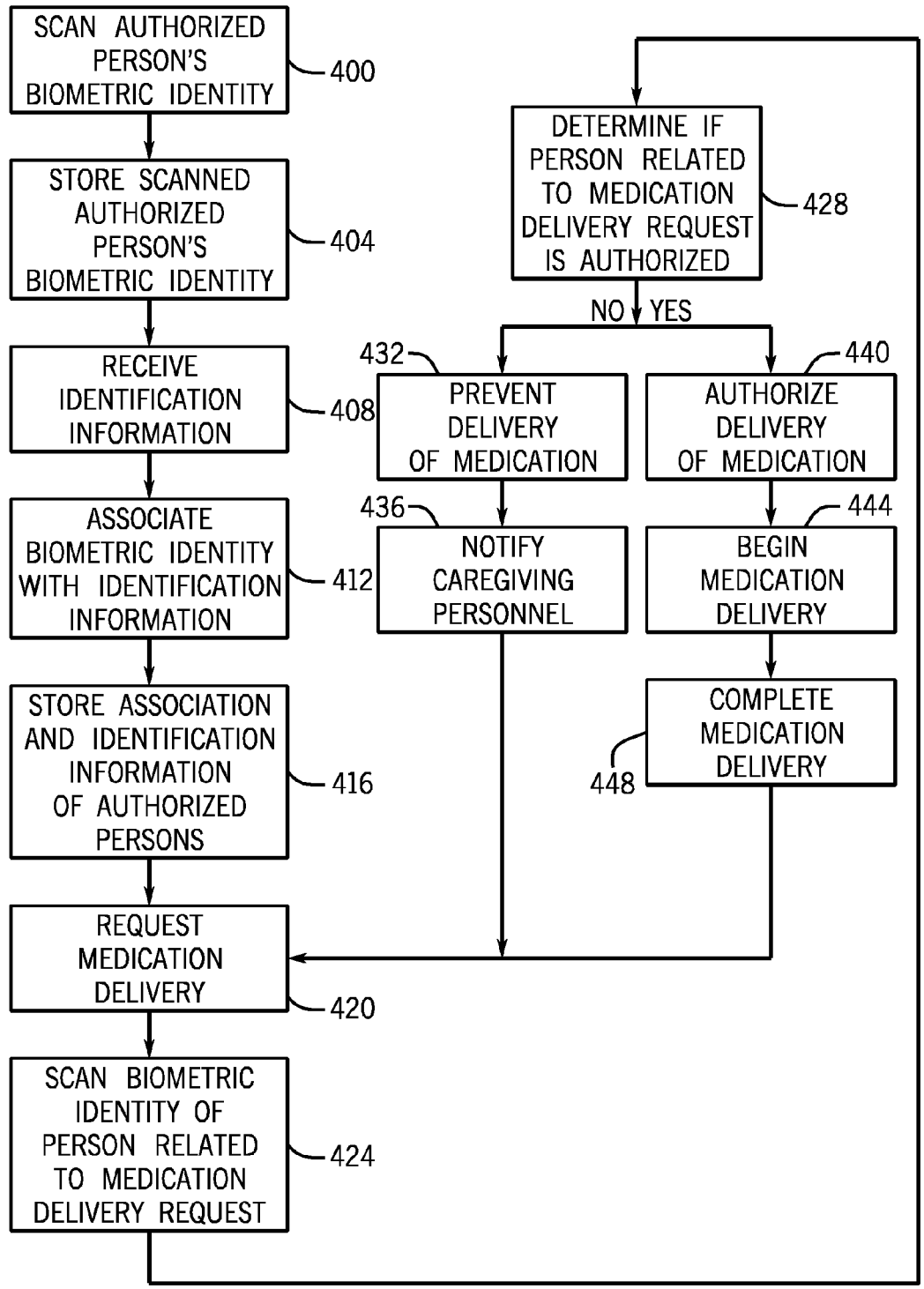
FIG. 4 is a flow chart of at least one embodiment of a system and method for delivering medication of the present invention.

Referring to FIG. 4, one embodiment of the method or process of delivering medication to a patient is shown in flow diagram format. Specifically, FIG. 4 shows some of the interactions between the various components of the system 200, 300, as well as some of the interactions between persons and the system 200, 300, patients and the system 200, 300, caregivers and the system 200, 300, and caregiver facility administrators and the system 200, 300. In a first step 400, a person can have at least one of their biometric identifiers scanned and/or read by a biometric receiver 33, 270, 370. In one embodiment, the biometric receiver 33, 270, 370 is a fingerprint reader and is used within a caregiving institution or facility, such as hospital. The biometric identifier can, thus, be a digital representation of a fingerprint of the person, such as a patient. The digital representation can be a digital image of the fingerprint. During the admission process, a hospital admission administrator or nurse can ask a patient to place the patient's finger on the fingerprint reader 33, 270, 370 to input a digital representation of one or more of the patient's fingerprints into the medication management/delivery system 200, 300. In a second step 404, the system then stores this biometric identity in a memory within the system. This information can be used to determine that the person, in this case the patient, is authorized to perform certain self-medication delivery administration actions, as will be described. In an embodiment where the person for which a biometric identify is obtained is not the patient, such as a caregiver, the system 200, 300 can store, for example in a memory associated with the central computer 202, 302, the biometric identity of the person as being authorized to perform certain medication delivery functions, as will described. In one embodiment, the central computer 202, 302, and medication management application/biometric application therein, receives this digital representation of the patient's fingerprint as an initial biometric signal from the biometric receiver 33, 270, 370, representing an initial biometric identifier of the person, and stores the initial biometric identifier to create the stored biometric identifier. Likewise, the biometric identifier could be stored in the memory 34 within the medical pump 10, instead or in addition to the central memory associated with the central computer 202, 302.

In a third step 408, prior to, proximate in time with, or after the biometric identity of the person is received by the system 200, 300, the system can also receive and store personal identification information for the person. In one embodiment, the caregiving personnel can request various personal identification information from the patient for entry into the system 200, 300, using a caregiving computer (not shown), such as a client computer in communication with the central computer 202, 302. In such an embodiment, instead of the biometric receiver 270, 370 being in communication with the central computer 202, 302 through a network interface 260, 360, the biometric receiver 270, 370 can be directly attached to the caregiving (client) computer, which is in turn in communication with the central computer 202, 302. The caregiving personnel can use this caregiving computer to enter the personal identification information of the person into the system 200, 300, such as by entering the personal identification information into the caregiving client computer for sending to and receipt by the central computer 202, 302, and the medication management application therein. For example, the caregiving personnel can request from the patient, and enter into the caregiving computer, personal identification information such as the patient's name, an address, a driver's license number, the patient's hair color, the patient's eye color, the patient's social security number. The caregiving personnel may also, or the central computer 202, 302 and medication management application 202, 302 may also, assign an anticipated room number and/or a personal ID number to the patient. The caregiving personnel may also further receive and enter a username, a password, and/or a photograph of the person. A digital camera may be in communication with the caregiver computer and/or central computer 202, 302, for receiving a digital photograph of the patient. Alternatively, an automated kiosk or computer terminal can be provided for a person, such as a patient, to enter their biometric identity and/or personal identification information into the system 200, 300 on their own, without the assistance of caregiving personnel, during an admission into a caregiving facility, for an outpatient surgery, or at some other time when capturing this information is appropriate.

In some settings, it will be known at the time of admission that the person, as a patient, will be provided with analgesic medication for pain relief, for example after a scheduled surgery, for delivery of the analgesic medication through a PCA request device in communication with a medical pump 10. In such circumstances, the caregiver personnel can arrange in advance for the proper authorizations to be stored in a memory, such as within the central computer 202, 302, for later use in authorizing a person to request a medication delivery of an analgesic medication. In one embodiment, as part of receiving and storing the initial biometric identifier and the personal identification information for the person, the patient themselves can use biometric receiver 33, 270, 370 to scan their own fingerprint at a kiosk or self-service computer terminal (not shown), as indicated above. The biometric receiver 33, 270, 370 can be built into the kiosk or self-service terminal, or can be attached to the kiosk or self-service terminal, for use by the patient to enter their own finger print into the system 200, 300, such as the central computer 202, 302 and medication management application therein. The patient can then use a keyboard and/or touch screen of the kiosk or self-service computer terminal to enter their own personal identification information into the system 200, 300, such as into the central computer 202, 302 and medication management application therein.

In a fourth step 412, the system 200, 300 can associate the received biometric identity of the person with the associated personal identification information. Specifically, any piece of, combination of, and/or all of the personal identification information can be associated with the biometric identifier, by, for example, the central computer 202, 302, and medication management application therein. In a fifth step 416, the system 200, 300 can store the association of the received biometric identity of the person with the associated personal identification information, as well as store the associated personal identification information. In one embodiment, the association and the associated personal identification information is stored within the central memory associated with the central computer 202, 302, by and for later retrieval and use by the medication management application, for at least performing medication delivery authorization functions, as described herein. In another embodiment, the association and the associated identification information can be stored within the memory 34 within the medical pump 10 for later retrieval and use as described herein.

In one embodiment, the initial biometric identifier or biometric identity of the person, whether the person is a caregiver, a patient, or some other person, can be associated with a particular patient and that patient's patient information, such as the patient's personal identification information. In particular, the biometric identifier stored in memory, such as the central memory of the central computer 202, 302, can be associated with the personal identification information of a patient that is also stored in memory, such as the central memory of the central computer 202, 302, by the medication management application. This association can be made at the time the patient is admitted to or checks into the caregiving facility, at the time a caregiver is assigned to a patient and/or to a patient's room, at the time a caregiver is assigned to implement a medication order, or at some other appropriate time. In one embodiment, the association can be used for designating which persons are authorized to deliver medication to the patient. For example, the association can be used to designate the patient themselves as being authorized to actuate a PCA request device 31 to self-administer an analgesic medication through the medical pump 10 to which the PCA request device 31 is attached.

As such, in a sixth step 420, a person can request a medication delivery, for themselves in an embodiment of a patient self-administering medication, and/or for a patient in the case of a caregiver delivering medication to the patient. As will be described, in one embodiment, the medication being delivered to a patient is an analgesic, and the analgesic is delivered to the patient utilizing the PCA request device 31 in communication with the medical pump 10, 210, 310. The medical pump 10 and/or the system 200, 300 can verify the identification of an authorized person for the delivery of the medication, prior to the medication delivery, such as a patient controlled analgesia delivery. Verifying the identification of an authorized person for delivering the medication can prevent unauthorized delivery of medication to the patient, such as by a relative of the patient, or even by an unauthorized caregiver. In a patient self-administration embodiment, the patient can request the medication delivery by actuating the PCA request device 31 attached to the medical pump 10, 210, 310, which generates a medication request signal. The medication request signal is communicated to the processor 30. The processor 30 and the medication delivery application 36 receive the medication request signal, which represents that the PCA request device 31 has been actuated.

In a seventh step 424, either prior to, contemporaneous with, or after the sixth step 420, the medical pump 10 and/or system 200, 300 can request the person that has requested the medication delivery to scan their biometric identity into the medical pump 10 and/or system 200, 300. The person related to the medication delivery request then scans their biometric identity into the medical pump 10 and/or system 200, 300. For example, a display or speaker output device 32 associated with the medical pump 10 can communicate to the person to place a specific finger (of a specific hand) on the biometric receiver 33 in an embodiment using a fingerprint scanner. The finger and hand of the person that is requested to be placed on the biometric receiver 33 will be the finger and hand that was used to previously scan and store such person's biometric identity into the system 200, 300 in steps 400 and 404, which the medical pump 10 can request and record as well within these prior steps. Once the person's biometric identity is scanned, biometric receiver 33 will generate a biometric identification signal for communication to the processor 30. The processor 30 and medication delivery application 36 receives the biometric identification signal from the biometric receiver 33, which represents a biometric identifier of the person.

In an eighth step 428, the medical pump 10 and/or the central computer 202, 302 will retrieve at least one stored biometric identifier and determine whether the received biometric identifier matches the at least one stored biometric identifier, for determining whether the person is authorized to initiate medication delivery to the patient using the medication delivery device, such as the medical pump 10. The stored biometric identifier can be retrieved from the local medical pump memory 34 and/or from the central memory of the central computer 202, 302, by the medication delivery application 36 and/or the medication management application, respectively. Likewise, the step of determining whether the received biometric identifier matches the at least one stored biometric identifier can be performed by the medication delivery application 36 and/or the medication management application. In one embodiment, the medical pump 10 and medication delivery application 36 communicates or transmits the received biometric identifier to the remote central computer 202, 302 and medication management application. The central computer 202, 302 and medication management application retrieves the stored biometric identifier from the remote central memory of the central computer 202, 302 and determines whether the received biometric identifier matches the at least one stored biometric identifier. As a result of this determination, the medication delivery application 36 and/or the medication management application generates a match result, which either represents that a match was determined or that no match was determined (a mismatch). Various strategies may be implemented to determine if a match exists. For example, the received biometric identifier can be compared to all of the biometric identifiers within a database of biometric identifiers stored within the memory, such as the central memory of the central computer 202, 302.

Alternatively, the received biometric identifier can be compared to a subset of all of the biometric identifiers within the database of biometric identifiers stored within the memory. Specifically, the subset can represent biometric identifiers of all patients within a hospital, can represent the biometric identifier(s) of patient(s) that are supposed to be in a particular patient room within a caregiving facility, can represent the biometric identifiers of all of caregivers within a caregiving facility, can represent the biometric identifier of all of the caregivers on a current shift within a caregiving facility, or can represent some other subset of biometric identifiers. The identification of the subset can be based on some additional known information related to the requested medication delivery, such as the patient room number or computer network address where the medication delivery is being requested, the current time that the medication delivery is being requested, the identification of the medication delivery device, such as the IP or MAC address of the medical pump 10 where the medication delivery is being requested, or some other additional known information related to the requested medication delivery. In one alternative embodiment, the central computer 202, 302 and medication management application receives the stored biometric identifier from a memory other than from the central memory of the central computer 202, 302, such as, for example, from the memory 34 within the medical pump 10, and/or from another memory. In one embodiment, the processor 30 and medication delivery application 36 of the medical pump 10 and/or the central computer 202, 302 and medication management application retrieves at least one stored biometric identifier representing at least one person that is authorized to actuate the PCA request device for the patient, and uses this stored biometric identifier to determine if the person whose biometric identifier was received through the biometric receiver 33 is authorized to initiate medication delivery to the patient using the PCA request device 31. This person will typically be the patient, but can also be a caregiver or other appropriately authorized person.

If the stored or initial biometric identifier does not match the received biometric identifier, as determined within the eighth step 428, the process proceeds to a ninth step 432, wherein the medical pump 10 and/or the system 200, 300 prevents delivery of the medication delivery to the patient. Specifically, in one embodiment, the medication management application at the central computer 202, 302 does the comparison of biometric identifiers and generates a match result representing that the stored biometric identifier does not match the received biometric identifier. The medication management application and central computer 202,302 will transmit the match result as a match result signal to the processor 30 and medication delivery application 36 of the medical pump 10. Of course, in another embodiment the medical pump 10 can do the comparison and provide a match result, match result signal, or delivery signal. In one embodiment, the match result signal can include a command for preventing the delivery of the medication delivery, such as a PCA medication delivery. This match result signal is received by the medication delivery application 36 and will then be used by the medication delivery application 36 to prevent delivery of the medication delivery, such as a PCA delivery, to the patient. Thus, the medical pump 10 will not provide a medication delivery.

In a tenth step 436, the medication delivery application 36 and/or medication management application 202, 302 transmit an alarm signal for notifying a caregiver of an unauthorized attempt to deliver medication to a patient. In one embodiment, the processor 30 and medication delivery application 36 will transmit an alarm signal to the output display device 32 as a visual alarm and/or to the output speaker device as an audible alarm. In a further embodiment, the medical pump 10 and medication delivery application 36 transmit an alarm signal to the central computer 202, 302 and medication management application, to the PDA 250, 350 being carried by a caregiver and/or to the caregiver computer 240, 340, which notifies one or more caregivers of the alarm and of the failed attempt to deliver medication to the patient. The process will continue and the medication delivery application 36 and/or the medication management application will return as indicated by connector B in FIG. 4 to await another request for a medication delivery at step 420.

If the stored or initial biometric identifier matches the received biometric identifier, as determined within the eighth step 428, the process proceeds to an alternative ninth step 440, wherein the medical pump 10 and/or the system 200, 300 authorize delivery of the medication delivery to the patient. Specifically, in one embodiment, the medication management application at the central computer 202, 302 does the comparison of biometric identifiers and generates a match result representing that the stored biometric identifier matches the received biometric identifier. The medication management application and central computer 202, 302 will transmit the match result as a match result signal or delivery signal to the processor 30 and medication delivery application 36 of the medical pump 10. Of course, in another embodiment the medical pump 10 can do the comparison and provide a match result, match result signal, or delivery signal. In one embodiment, the match result signal can include a command for authorizing the delivery of the medication delivery, such as a PCA medication delivery. This match result signal is received by the medication delivery application 36 and will then be used by the medication delivery application 36 to initiate delivery of the medication delivery, such as a PCA delivery, to the patient. Of course, other determinations can be performed by the medication delivery application 36 and/or the medication management application prior to initiating a medication delivery, such as determining the amount of time that has elapsed since the last request for a medication delivery or the completion of the last medication delivery, determining whether the patient's cardiopulmonary conditions are adequate to receive a medication delivery, performing one or more of five rights checking functions, and/or other determinations. If one or more of these additional predetermined criteria have been satisfied, then the medication delivery may not be authorized.

In an alternative tenth step 444, the medication delivery application 36 and medical pump 10 begin the requested medication delivery. In one embodiment, the processor 30 and medication delivery application 36 will direct the power supply 40 to provide power to the pump drive mechanism 14 for delivering the medication to the patient. In an eleventh step 448, once the medication delivery has completed, and/or other predetermined criteria have been met, the medication delivery application 36 and/or the medication management application will return as indicated by connector B in FIG. 4 to await another request for a medication delivery at step 420.

The delivery of medication can include at least programming and starting a continuous infusion of medication using a medical pump 10, 210, 310, providing a bolus delivery of medication using an infusion pump 10, 210, 310, or another type of delivery of medication to the patient. In the case of patient controlled analgesia, the biometric identity matching feature is useful for determining that it is the patient requesting a bolus delivery of pain medication, rather than a friend or relative conducting PCA by proxy.

Figure 10:
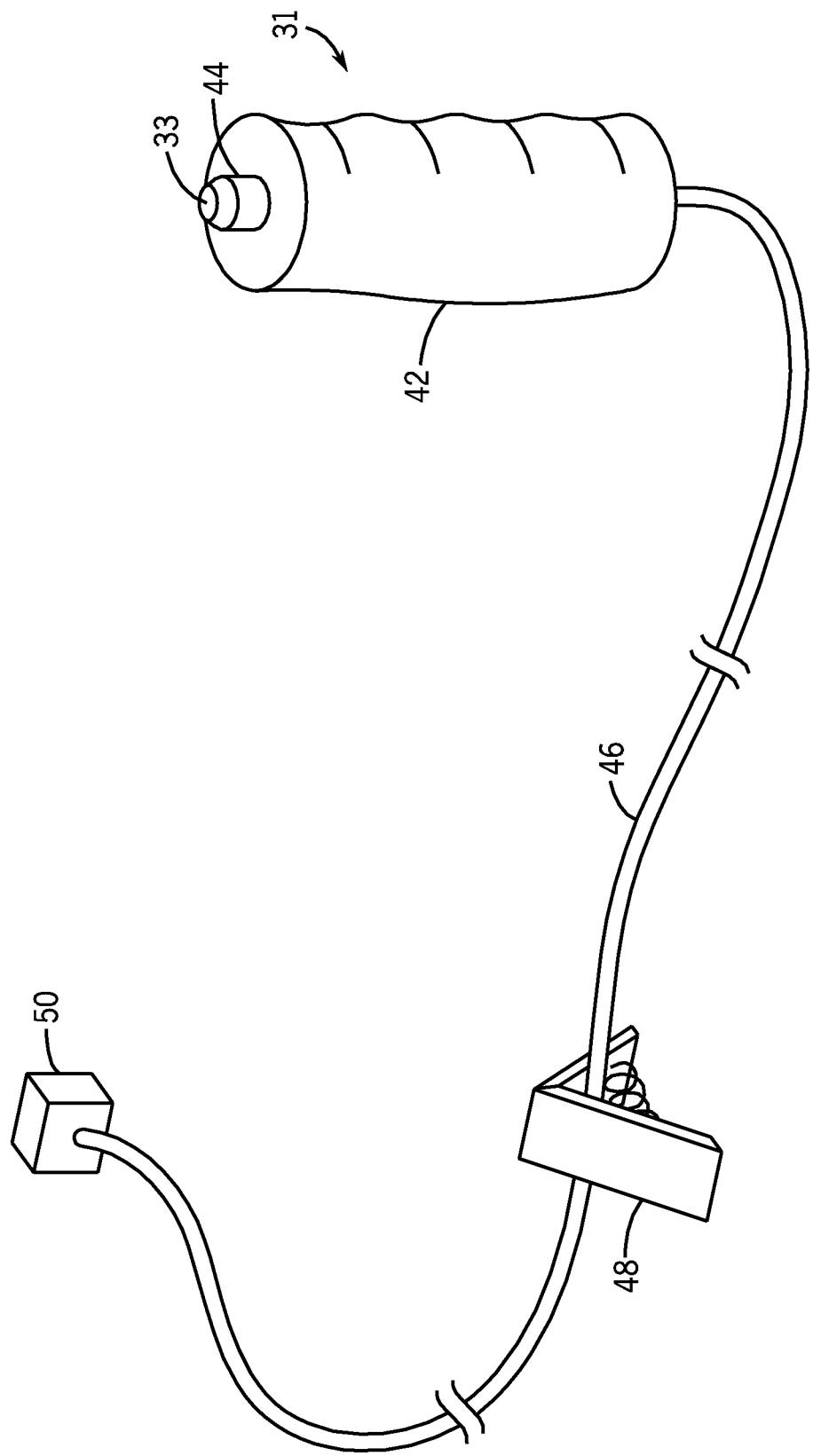
FIG. 10 illustrates one embodiment of a patient controlled analgesia (PCA) request device that has an integrated biometric sensor.

The biometric receivers described herein can be a single biometric receiver, such as a finger print reader operatively connected to the processor 30 within the medical pump 10. An example of such a fingerprint scanner biometric receiver 33 integrated into a PCA request device 31 or demand pendant is illustrated in FIG. 10. The PCA request device 31 has a body 42 that houses an actuation button 44 and is connected to the medication delivery pump 10 by a communication and power cable 46 with a suitable connector 50. The fingerprint scanner biometric receiver 33 is disposed on an exposed end the button 44 and is positioned so that it will be operatively contacted whenever the button 44 is pushed. For other types of biometric receivers, this invention contemplates that the receiver is at least carried or supported by the same housing 42 as the PCA request device 31 (or a PDA or scanner acting in that capacity) and is adapted to be operatively engaged through hardware or software limitations whenever the requestor actuates the request device. Alternatively, the biometric receivers described herein can be a single biometric receiver 270, 370, such as a finger print reader operatively connected to the central computer 202, 302, through a network interface bridge 260, 360. In a further embodiment, there can be a plurality of biometric receivers, as shown and described in relation to FIGS. 1, 2, and 3. Specifically, a first biometric receiver 270, 370 is in communication with a communications network interface 260, 360, which is in communication with the central computer 202, 302 and medication management application, which stores the initial biometric identifier and the associated identification information in the central memory, and a second biometric receiver 33 is in communication with the processor 30 or the medical pump 10 for receiving the received biometric identifier.

In one embodiment of the present invention, a person will request a medication delivery, such a for example, by actuating the PCA request device 31, the processor 30 and medication delivery application 36 will receive the associated medication request signal from the PCA request device 31, and this will trigger the processor 30 and medication delivery application 36 to transmit to transmit a biometric scan request signal. The biometric scan request signal can prompt the person to scan their biometric identity, such as their fingerprint, using the biometric receiver 33. The scan occurs and the processor 30 and medication delivery application 36 receives a biometric identifier from the biometric receiver 33. Alternatively, the person is first prompted to scan their biometric identity, such as the person being prompted by the processor 30 and medication delivery application 36 generating and transmitting a prompt to an output display 32 or output speaker 32 to scan the person's fingerprint using the biometric receiver 33. The person scans their biometric identity and the processor 30 and medication delivery application 36 receives the person's biometric identity, and the medication delivery application 36 and/or the medication management application then determines whether the person is authorized to request a medication delivery. Specifically, if the received biometric identifier matches or in some predetermined way corresponds to the stored biometric identifier, then the medication delivery application 36 enables the medical pump 10 to receive a medication delivery request. For example, in one embodiment, if the received biometric identifier matches the stored biometric identifier, then the medication delivery application 36 can enable the PCA request device 31 to receive a medication request for a predetermined period of time, such as for thirty (30) seconds, after which time the PCA request device 31 in no longer enabled. The medical pump 10 and/or the PCA request device can be configured to include an LED or other light source (not shown), such that when the PCA request device is enabled, the light source is energized and lit up until the PCA request device 31 is no longer enabled. The person can then request the medication delivery, such as by actuating the enabled PCA request device 31, and the processor 30 and medication delivery application 36 will then receive the medication request signal from the PCA request device, and the processor 30 and medication delivery application 36 will then transmit a delivery signal for the medication delivery if the medication request signal is received within the predetermined limited period of time.

As indicated above, when a person is checking into a caregiving facility, the person's biometric identity and personal identification information can be obtained, received, and stored by the system 200, 300. However, it may not be known that at that time that a biometric identity associated with the person's personal identification information is needed, or that the person will need certain medication delivery which requires biometric scanning and identity authorization using biometric scanning, in which case the biometric identity is not received or stored. It may be that the caregiver just forgets to obtain the biometric identity of the person. In such circumstances, and others, the system 200, 300 can be configured to receive the initial biometric identity from the biometric receiver 33 attached to the medical pump 10 that is being used or will be used to deliver medication to the person (patient). The medication management application and the central computer 202, 302 can be configured to receive the initial biometric identity from the medical pump 10 along with a medication delivery device identification signal representing a medication delivery device ID, such as the medical pump ID. The medication management application and the central computer 202, 302 can be configured to associate the medication delivery device ID with the initial biometric identifier, store the initial biometric identifier, and store the association between the stored biometric identifier and the medication delivery device ID, along with the other personal identification information of the person, as a part of the person/patient record or at another location within the central memory of the central computer 202, 302. This functionality provides for central tracking of established associations between medical pumps 10, biometric identifiers and personal identification information, at least a part of which has been established at the medical pumps 10.

In one embodiment, the biometric receiver includes means for attaching it to the patient or an article worn by the patient. For example, as best seen in FIG. 10, the biometric receiver or the PCA request device 31 to which it is attached can optionally include a clip, a strap, a clamp, a fastener, a clasp, a pin, a tie, a buckle, and/or a hook or mechanism 48 which includes one or more of these devices, for attaching the biometric receiver 33, 270, 370 to the patient or an article worn by the patient. In one particular embodiment, the PCA request device 31 and the biometric receiver 33, 270, 370 are combined as a unitary device or apparatus, which is connectable to medical pump 10 or made integral with the medical pump 10.

Figure 5:
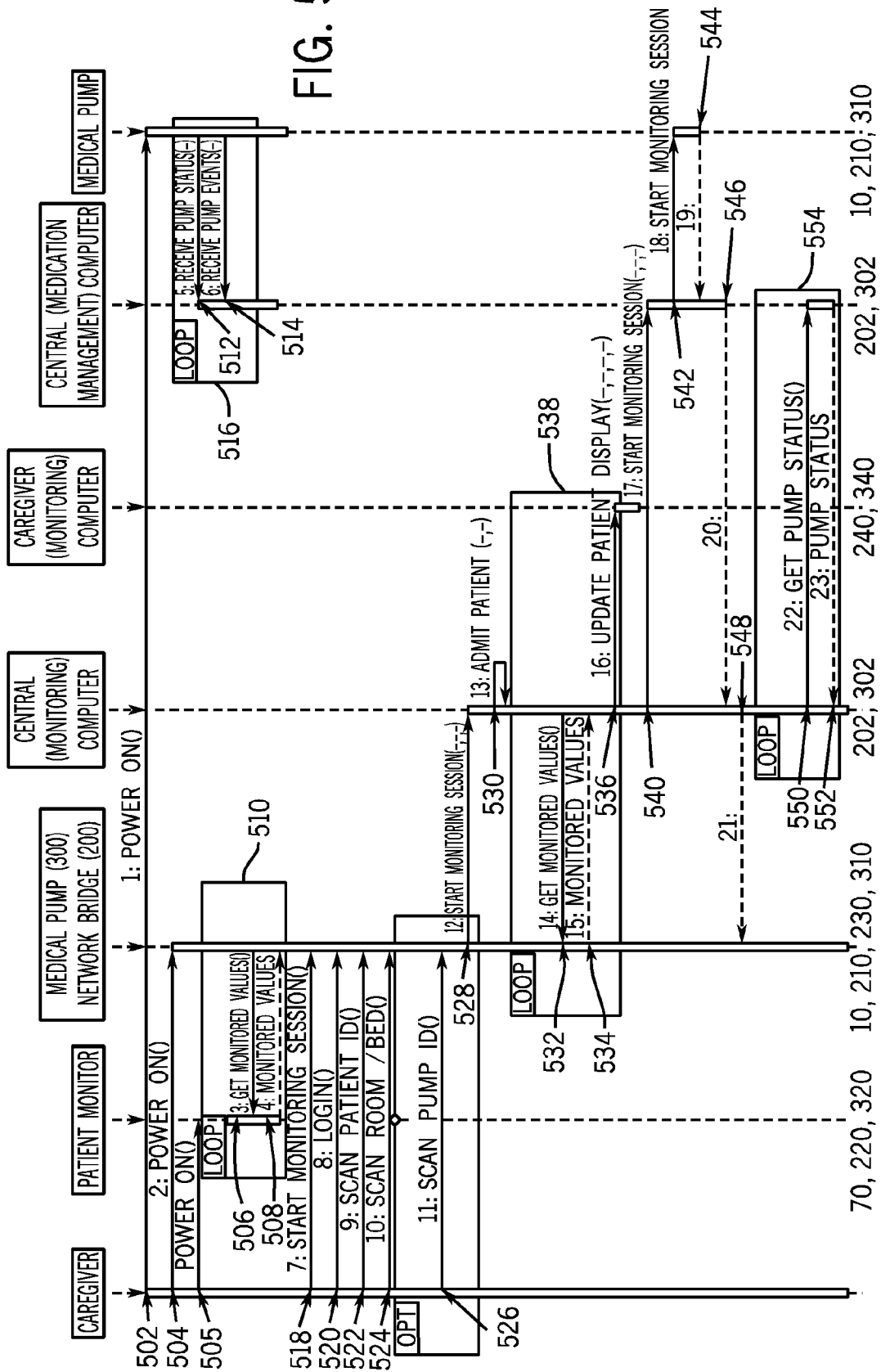
FIG. 5 is a flow diagram of one embodiment of implementing patient condition monitoring within the present invention.
Figure 6:
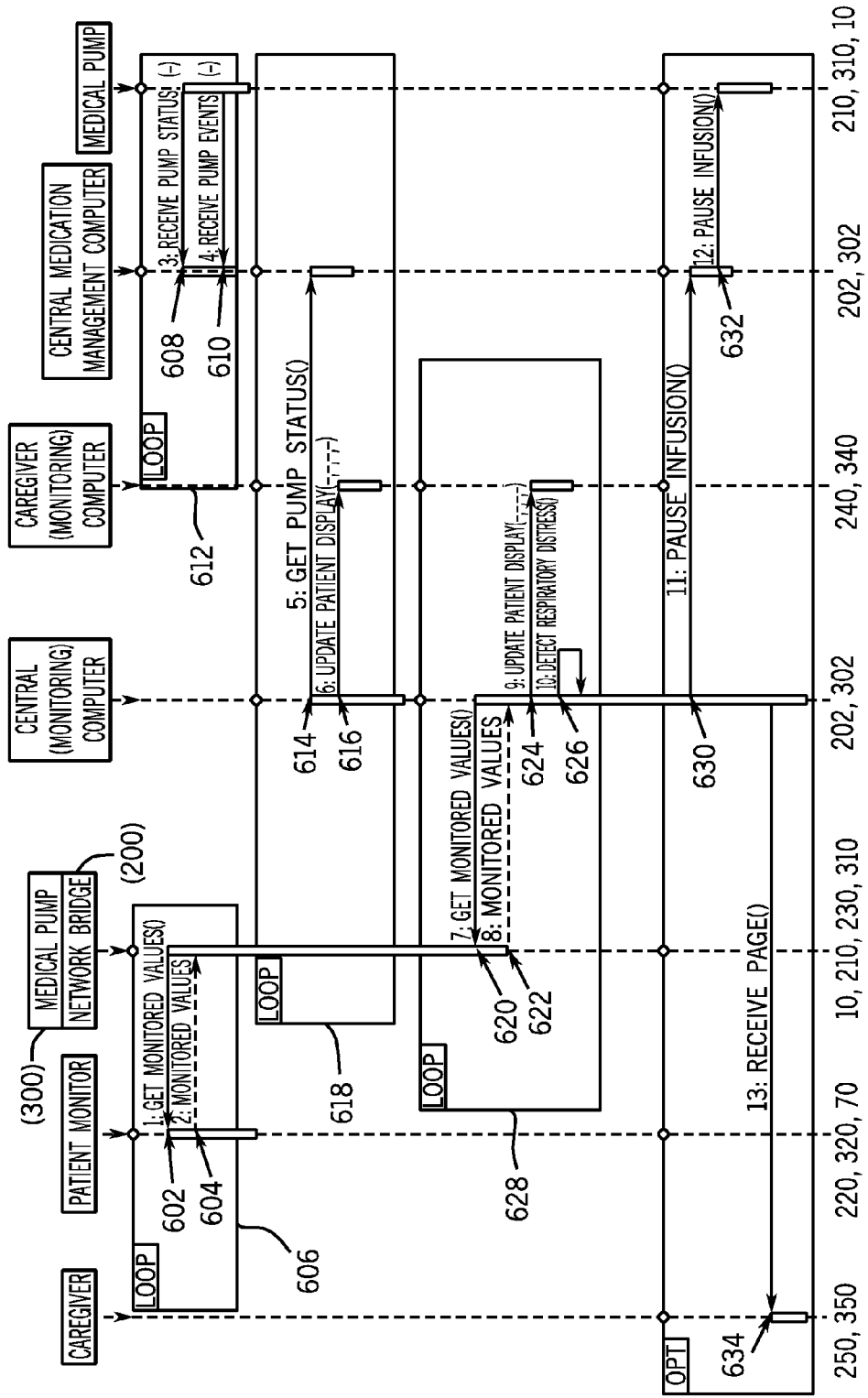
FIG. 6 is a flow diagram of implementing another embodiment of patient condition monitoring within the present invention.

The present invention is also directed to a patient condition monitoring and notification system and method that monitors patient conditions and notifies caregiving personnel of pump and patient condition information. FIGS. 2 and 3 depict two exemplary embodiments of a patient condition monitoring and notification system 200, 300. Referring to FIGS. 5 and 6, further specific embodiments of the patient condition monitoring and notification systems 200, 300 and methods are shown and will now be described. Toward the top and bottom of each of FIGS. 5 and 6, designations are provided that generally refer to the elements shown and described in relation to FIGS. 1, 2 and 3. In the patient condition monitoring and notification system 200, the patient condition monitor 220 in FIG. 2 communicates with the central computer 202 through the network interface or bridge 230, and therefore one column in FIGS. 5 and 6 is designated as "Network Bridge" 230 (listed as the bottom of that column) for that embodiment. Alternatively, in the patient condition monitoring and notification system 300, the patient condition monitor 70, 320 in FIG. 3 communicates with the central computer 302 through the medical pump 310, and therefore that same column is also designated as "Medical Pump" 310 (listed as the bottom of that column) in FIGS. 5 and 6 for this alternative embodiment. Each identified column indicates where a manual action and/or an automated action generally originates and/or is received. Examples of some manual actions are a caregiver pressing a button, using a bar code or other type of scanner (RFID, etc.), or reading information in a display. Examples of some automated actions are transmitting/receiving a command or transmitting/receiving patient condition information. For the purposes of describing one or more embodiments of the patient condition monitoring and notification system 200, 300, FIGS. 5 and 6 from left to right refer to a caregiver (with a PDA 250, 350 in FIG. 6), a patient (condition) monitor 220, 320, 70, a medical pump 10, 210, 310 or network bridge 230, a central (monitoring) computer 202, 302, a caregiver (monitoring) computer or caregiving computer 240, 340, a central (medication management) computer 202, 302, and the medical pump 10, 210, 310 previously mentioned. For both of these particular embodiments, the central computers 202, 302 are shown as at least functionally separated into a central (monitoring) computer 202, 302 and a central (medication management) computer 202, 302. As described herein, a single central computer 202, 302 can have both a medication management application and a central patient monitoring application thereon, or the functions can be separated and distributed onto multiple computers.

One of the tasks which a caregiver can perform in relation to the embodiments of FIGS. 5 and 6 is to establish a monitoring session for monitoring patient conditions and/or medical pump status information. In establishing a patient condition/medical pump monitoring session, a caregiver will perform several steps which are also performed in performing five rights checking functions, as one of skill would understand from the present description in combination with information that is already incorporated herein by reference. Specifically referring to FIG. 5, in a first step 502, the caregiver powers on the medical pump 10, 210, 310. In a second step 504, the caregiver powers on the network bridge 230, if present. The patient monitor 70, 220, 320 will also need to be connected to a patient and powered on in step 505. Once this occurs, the patient (condition) monitor 70, 220, 320 will then begin receiving patient condition signals at the patient (condition) monitor for monitoring at least one condition of the patient.

To obtain current patient condition information, in a third step 506, the medical pump 10, 310/network bridge 230 transmits a patient condition information request to the patient monitor 70, 220, 320 to obtain the current patient condition information for a patient. The patient condition information can include, but is not limited to, $ETCO_2$, $SpO_2$, respiratory rate, heart rate, and other patient condition information. Other patient condition information can include monitor alarms, alerts or similar information regarding the patient's condition. The patient monitor 70, 220, 320 receives the patient condition information request to obtain the current patient condition information for the patient, and in a fourth step 508, transmits the current patient condition information for the patient to the medical pump 10, 310/network bridge 230. The medical pump 10, 310/network bridge 230 receives the current patient condition information and can store the current patient condition information in a memory, such as the memory 34 in the case of the medical pump 10, 210, 310. In one embodiment, the medical pump 10, 310/network bridge 230 will only store patient values for current patient condition information when a value has changed. Thus, previously obtained patient condition information values will remain in the memory if such the current values received from the patient monitor 70, 220, 320 have not changed. The third and fourth steps 506, 508 can combine to form a current patient condition information loop 510, which can continuously be performed at regular intervals within a programming loop for making sure the medical pump 10, 310/network bridge 230 have the most current patient condition information values. Thus, in one embodiment, the medical pump 10, 310 receives patient condition information from the patient (condition) monitor 70, 320, representing at least one condition of the patient.

The medical pump 10, 210, 310 tracks and stores medication delivery status information at the medical pump 10, 210, 310, representing the status of a medication delivery provided by the medical pump to a patient. To provide this current medical pump status information in one embodiment, in a fifth step 512, the medical pump 210, 310 transmits current medical pump status information to the central (medication management) computer 202, 302. To provide current medical pump event information at the central computer 202, 302, in one embodiment, in a sixth step 514, the medical pump 10, 210, 310 transmits current medical pump event information to the central (medication management) computer 202, 302. The central computer 202, 302 for medication management then stores this information in the central memory for use within the medication management and delivery processes. Medical pump status information can include whether an active delivery of medication is taking place, the current rate of the delivery, how long since the delivery began, and other current state information related to the operation of the medical pump and its programmed infusion. Medical pump event information can include whether any alarms, alerts, stops/pauses/resumptions (whether manual or automatic) have occurred since the last communication, whether an occlusion has taken place, whether power was lost to the medical pump 10, 210, 210, in addition to other historical information about the operation of the medical pump. Status information and/or medication delivery status information is used herein to refer to at least medical pump status information, medical pump event information, and other information.

Alternatively, to obtain current medical pump status or event information, the central (medication management) computer 202, 302 can transmit a medical pump update request signal to the medical pump 10, 210, 310 to obtain current medical pump status or event information. The medical pump 10, 210, 310 receives the medical pump update request to obtain current medical pump status or event information, and in turn retrieves the current medical pump status or event information at the medical pump 10, 210, 310. The medical pump 10, 210, 310 then transmits the current medical pump status or event information to the central (medication management) computer 202, 302. The central computer 202, 302 receives the current medical pump status or event information and can store the current medical pump status or event information in the central memory. In one embodiment, the central computer 202, 302 will only store medical pump values for current medical pump status information when a value has changed. Thus, previously obtained medical pump status information values will remain in the central memory if such the current values received from the medical pump 10, 210, 310 have not changed. The fifth and sixth steps 512, 514, and/or the alternative steps described therefor, can combine to form a current medical pump status information loop 516, which can continuously be performed at regular intervals within a programming loop for making sure the central (medication management) computer 202, 302 and central memory, have the most current medical pump status information values and event information from the medical pump 10, 210, 310.

In one embodiment, the current patient condition information loop 510, current medical pump status information loop 516, and/or other loops described herein, are performed at start up. Startup or power on may be a useful time to perform these and other loops, for example in a situation when power is lost at the medical pump 10, 210, 310/network bridge 230 during a medication delivery. Performing the current patient condition information loop 510 first, or proximate in time to power on, will make sure that current patient condition information is ready to be communicated to the central (monitoring) computer from the medical pump 10, 210, 310/network bridge 230 when power is returned to these devices. Likewise, performing the current medical pump status information loop 516 first, or proximate in time to power on, will make sure that current medical pump status information is communicated to and received by the central (medication delivery) computer 202, 302 from the medical pump 10, 210, 310 when power is returned to this device.

Returning to the process of establishing a monitoring session for monitoring patient conditions, in a seventh step 518, the caregiver provides an input to the medical pump 10, 210, 310/network bridge 230, such as pressing a button on a touch screen interface display 32, to start a monitoring session for the patient. The input provided by the caregiver can be provided through a main interface screen or subscreen displayed on the interface display, such as a display 32 of the medical pump 10, 210, 310 or of the client bridge 230 (not shown). In one embodiment, a monitoring session can be defined as a period of time having a beginning and an end in between which the patient monitor 70, 220, 320 obtains patient condition information, the patient condition information is communicated to caregiving computer 240, 340, and the caregiving computer 240, 340 displays the patient condition information on an associated display interface screen. The medical pump 10, 210, 310/network bridge 230 or the caregiving computer 240, 340, and software applications therein, can then display a request for the caregiver to provide login information, such as a username and password. The displayed request for the caregiver to provide login information could also be in the form of the caregiver being requested to scan a barcode or other machine readable identifier, such as a barcode on the caregiver's badge or identification card.

In an eighth step 520, the caregiver provides an input to the medical pump 10, 210, 310/network bridge 230 or caregiving computer 240, 340 to provide login information. For example, the caregiver can enter their username and password into a touchscreen display of the medical pump 10, 210, 310/network bridge 230 or into the caregiving computer 240, 340. In one embodiment, the caregiver can scan a barcode on the caregiver's badge or identification card using a barcode reader 35 attached to the medical pump 310/network bridge 230, or can perform some other method to enter their login information. In one embodiment (not shown), the login and other identification information entered and/or scanned at the medical pump 10, 210, 310/client bridge 230 can be communicated to the central computer 202, 302, can be verified by the central computer 202, 302 and software application(s) therein, and the verification can be communicated back to the medical pump 10, 210, 310/client bridge 230 or caregiving computer 240, 340.

In an ninth step 522, the caregiver provides an input to the medical pump 10, 210, 310/network bridge 230 to provide patient identification information. For example, the caregiver can enter a patient's name and/or identification number through a touchscreen display of the medical pump 10, 210, 310/network bridge 230, can scan a barcode on the patient's wristband using a barcode reader 35 attached to the medical pump 10, 210, 310/network bridge 230 or the caregiving computer 240, 340, or can perform some other method to enter the patient ID. In one embodiment (not shown), the patient ID and other identification information entered and/or scanned at the medical pump 10, 210, 310/client bridge 230 can be communicated to the central computer 202, 302, can be verified by the central computer 202, 302 and software application(s) therein, and the verification can be communicated back to the medical pump 10, 210, 310/client bridge 230 or caregiving computer 240, 340.

In an tenth step 524, the caregiver provides an input to the medical pump 10, 210, 310/network bridge 230 to provide patient bed and/or room identification information. For example, the caregiver can enter a patient's bed/room identification number through a touchscreen display of the medical pump 10, 210, 310/network bridge 230, can scan a barcode on or associated with the bed/room using a barcode reader 35 attached to the medical pump 10, 210, 310/network bridge 230 or the caregiving computer 240, 340, or can perform some other method to enter the patient's bed/room identification information. In one embodiment (not shown), the patient's bed/room ID and other identification information entered and/or scanned at the medical pump 10, 210, 310/client bridge 230 can be communicated to the central computer 202, 302, can be verified by the central computer 202, 302 and software application(s) therein, and the verification can be communicated back to the medical pump 10, 210, 310/client bridge 230 or caregiving computer 240, 340.

In an eleventh step 526, the caregiver provides an input to the medical pump 10, 210, 310/network bridge 230 to provide the medical pump identification information. For example, the caregiver can enter a medical pump identification number through a touchscreen display of the medical pump 10, 210, 310/network bridge 230, can scan a barcode on or associated with the medical pump using a barcode reader 35 attached to the medical pump 10, 210, 310/network bridge 230, or can perform some other method to enter the medical pump identification information. In one embodiment (not shown), the medical pump ID and other identification information entered and/or scanned at the medical pump 10, 210, 310/client bridge 230 can be communicated to the central computer 202, 302, can be verified by the central computer 202, 302 and software application(s) therein, and the verification can be communicated back to the medical pump 310/client bridge 230 or caregiving computer 240, 340.

In a twelfth step 528, the medical pump 10, 210, 310/network bridge 230 transmits a start monitoring session signal to the central (monitoring) computer 202, 302 to communicate to request that a monitoring session be started. In one embodiment the start monitoring session signal communicated to and received by the central (monitoring) computer 202, 302 includes identification information for a particular caregiver, a particular patient, a particular room/bed, and/or a particular medical pump, in order to provide the central (monitoring) computer 202, 302 with sufficient information to identify future received patient condition information and/or medical pump status and event information. In a thirteenth step 530, the central (monitoring) computer 202, 302 and computer software therein can admit or add a particular patient into the patient condition monitoring application for establishing a monitoring session for that patient. Several verifications can be performed prior to, during or after this step, such as verifying identification information for the particular caregiver, particular patient, particular room/bed, and/or particular medical pump.

To obtain and display current patient condition information, the central computer receives patient condition information that was previously received by the patient condition monitor. Specifically, in a fourteenth step 532, in one embodiment, the central (monitoring) computer 202, 302 transmits a request to the medical pump 10, 210, 310/network bridge 230 to get or obtain monitored values. In one embodiment, the central (monitoring) computer 202, 302 transmits a patient condition update request signal to obtain patient condition information and/or transmits a patient condition information request to the medical pump 10, 210, 310/network bridge 230 to obtain the current patient condition information for a patient. As mentioned, the patient condition information can include, but is not limited to, $EtCO_2$, $SpO_2$, respiratory rate, heart rate, and other patient condition information. Other patient condition information can include monitor alarms, alerts or similar information regarding the patient's condition. The medical pump 10, 210, 310/network bridge 230 receives the patient condition update/information request signal to obtain the current patient condition information for the patient, and in a fifteenth step 534, retrieves the current patient condition information and transmits the current patient condition information for the patient to the central (monitoring) computer 202, 302. The central (monitoring) computer 202, 302 receives the current patient condition information and can store the current patient condition information in a memory, such as the central memory of the central computer 202, 302. In one embodiment, the central (monitoring) computer 202, 302 will only store patient values for current patient condition information when a value has changed. Thus, previously obtained patient condition information values will remain in the central memory if such the current values received from the medical pump 10, 210, 310/network bridge 230 have not changed.

The patient condition information is transmitted from the central computer 202, 302 to the caregiving computer 240, 340, and the caregiving computer 240, 340 receives and displays the patient condition information at the caregiving computer 240, 340. Specifically, in a sixteenth step 536, in one embodiment, the central (monitoring) computer 202, 302 transmits the received/current patient condition information to the caregiver (monitoring) computer or caregiving computer 240, 340. As described, one example of where a caregiver (monitoring) computer or caregiving computer 240, 340 is used and located is at a nurses' station within a hospital. The caregiver (monitoring) computer or caregiving computer 240, 340 displays the received/current patient condition information within an interface screen for viewing by one or more caregivers. The fourteenth, fifteenth and sixteenth steps 532, 534, 536 can combine to form a current patient condition information display loop 538, which can continuously be performed at regular intervals within a programming loop for making sure the central (monitoring) computer 202, 302 has received the most current patient condition information values and for making sure that the most current patient condition information values are displayed on the caregiver (monitoring) computer or caregiving computer 240, 340.

In a seventeenth step 540, the central (monitoring) computer 202, 302 transmits a start monitoring session signal to the central (medication management) computer 202, 302 to communicate to request that a monitoring session be started at the central (medication management) computer 202, 302. In one embodiment the start monitoring session signal communicated to and received by the central (medication management) computer 202, 302 includes identification information for a particular caregiver, a particular patient, a particular room/bed, and/or a particular medical pump, in order to provide the central (medication management) computer 202, 302 with sufficient information to identify future received patient condition information and/or medical pump status information, and to store such information in the central memory, if not already stored in the central memory. In a eighteenth step 542, the central (medication management) computer 202, 302 transmits a start monitoring session signal to the medical pump 10, 210, 310 to request that a monitoring session be started at medical pump 10, 210, 310. In one embodiment, the medical pump 10, 210, 310 receives the start monitoring session signal and in turn begins the current medical pump status information loop 516. In nineteenth 544, twentieth 546, and twenty-first 548 steps, confirmation signals can be sent to the central (medication management) computer 202, 302, to the central (monitoring) computer 202, 302, and to the network bridge 230 (in system 200), respectively, to confirm that a monitoring session should begin or is underway.

In a twenty-second step 550, the central (monitoring) computer 202, 302 transmits a request to the central (medication management) computer 202, 302 to get or obtain monitored values. In one embodiment, the central (monitoring) computer 202, 302 transmits a request to the central (medication management) computer 292, 302 obtain current medical pump status information that was already obtained by the central (medication management) computer 290, 302 from the medical pump 10, 210, 310 as a result of the performance of the current medical pump status information loop 516. The central (medication management) computer 290, 302 receives this request and in a twenty-third step 552, transmits the current medical pump status information (including event information), that was already obtained by the central (medication management) computer 290, 302 from the medical pump 10, 210, to the central (monitoring) computer 202, 302. The twenty-second and the twenty-third steps 550, 552 can combine to form a current medical pump status information display loop 554, which can continuously be performed at regular intervals within a programming loop for making sure the central (monitoring) computer 202, 302 has received the most current medical pump status information and for making sure that the most current medical pump status information values are displayed on the caregiver (monitoring) computer or caregiving computer 240, 340. This can be accomplished by the sixteenth step 536, wherein the central (monitoring) computer 202, 302 also transmits the received/current medical pump status information to the caregiver (monitoring) computer or caregiving computer 240, 340. As described, one example of where a caregiver (monitoring) computer or caregiving computer 240, 340 is used and located is at a nurses' station within a hospital. The caregiver (monitoring) computer or caregiving computer 240, 340 then displays the received/current medical pump status information within an interface screen for viewing by one or more caregivers.

Another of the tasks that can be performed in relation to the embodiments of FIGS. 5 and 6 is to notify a caregiver using a PDA of particular patient condition information and/or medical pump status or event information that the system is set up to communicate to a PDA, and therefore to a caregiver using the PDA. Referring to FIG. 6, similar to the current patient condition information loop 510 as described in relation to FIG. 5, to obtain current patient condition information, in a first step 602, the medical pump 10, 210, 310/network bridge 230 transmits a patient condition information request to the patient monitor 70, 220, 320 to obtain the current patient condition information for a patient. As described, the patient condition information can include, but is not limited to, $EtCO_2$, $SpO_2$, respiratory rate, heart rate, and other patient condition information. Other patient condition information can include monitor alarms, alerts or similar information regarding the patient's condition. Thus, in one embodiment, one or more respiratory condition signals are received and measured by the patient condition monitor 70, 220, 320, representing a respiratory level of the patient. The patient monitor 70, 220, 320 receives the patient condition information request to obtain the current patient condition information for the patient, and in a second step 604, transmits the current patient condition information for the patient to the medical pump 10, 210, 310/network bridge 230. The medical pump 310/network bridge 230 receives the current patient condition information and can store the current patient condition information in a memory, such as the memory 34 in the case of the medical pump 10, 210, 310. In one embodiment, the medical pump 10, 210, 310/network bridge 230 will only store patient values for current patient condition information when a value has changed. Thus, previously obtained patient condition information values will remain in the memory if such the current values received from the patient monitor 70, 220, 320 have not changed. The first and second steps 602, 604 can combine to form a current patient condition information loop 606, which can continuously be performed at regular intervals within a programming loop for making sure the medical pump 10, 210, 310/network bridge 230 have the most current patient condition information values. Thus, in one embodiment, the medical pump 10, 210, 310 receives patient condition information from the patient (condition) monitor 70, 320, representing at least one condition of the patient.

Similar to the current medical pump status information loop 516, described in relation to FIG. 5, to provide current medical pump status information in one embodiment, in a third step 608, the medical pump 10, 210, 310 transmits current medical pump status information to the central (medication management) computer 202, 302. To obtain current medical pump event information at the central computer 202, 302, in one embodiment, in a fourth step 610, the medical pump 10, 210, 310 transmits current medical pump event information to the central (medication management) computer 202, 302. The central computer 202, 302 for medication management then stores this information in the central memory for use within the medication management and delivery processes. Medical pump status information can include whether an active delivery of medication is taking place, the rate of the delivery, how long since the delivery began, among other medical pump status information. Medical pump event information can include whether any alarms or alerts have issued since the last communication, whether an occlusion has taken place, whether power was lost to the medical pump 10, 210, 210, among other medical pump event information. Status information and/or medication delivery status information is used herein to refer to at least medical pump status information, medical pump event information, and/or other status and/or event information.

Alternatively, to obtain current medical pump status information, the central (medication management) computer 202, 302 can transmit a medical pump update request signal to the medical pump 10, 210, 310 to obtain current medical pump status information. The medical pump 10, 210, 310 receives the medical pump update request to obtain current medical pump status information, and in turn retrieves the current medical pump information at the medical pump 10, 210, 310. The medical pump 10, 210, 310 then transmits the current medical pump status information to the central (medication management) computer 202, 302. The central computer 202, 302 receives the current medical pump status information and can store the current medical pump status information in the central memory. In one embodiment, the central computer 202, 302 will only store medical pump values for current medical pump status information when a value has changed. Thus, previously obtained medical pump status information values will remain in the central memory if such the current values received from the medical pump 10, 210, 310 have not changed. The third and fourth steps 608, 610, and/or the alternative steps described therefor, can combine to form a current medical pump status information loop 612, which can continuously be performed at regular intervals within a programming loop for making sure the central (medication management) computer 202, 302 and central memory have the most current medical pump status information values from the medical pump 10, 210, 310.

Similar to the current medical pump status information display loop 554 and the current patient condition information display loop 538 described in relation to FIG. 5, in a fifth step 614, the central (monitoring) computer 202, 302 transmits a request to the central (medication management) computer 202, 302 to get or obtain monitored values. In one embodiment, the central (monitoring) computer 202, 302 transmits a request to the central (medication management) computer 202, 302 to obtain current medical pump status information that was already obtained by the central (medication management) computer 202, 302 from the medical pump 10, 210, 310 as a result of the performance of a loop 612 similar to the current medical pump status information loop 516 described in relation to FIG. 5. The central (medication management) computer 202, 302 receives this request and transmits the current medical pump status information that was already obtained by the central (medication management) computer 202, 302 from the medical pump 10, 210, 310 to the central (monitoring) computer 202, 302. In a sixth step 616, the central (monitoring) computer 202, 302 transmits the received/current patient condition information to the caregiver (monitoring) computer or caregiving computer 240, 340. As described, one example of where a caregiver (monitoring) computer or caregiving computer 240, 340 is used and located is at a nurses' station within a hospital. The caregiver (monitoring) computer or caregiving computer 240, 340 then displays the received/current patient condition information within an interface screen for viewing by one or more caregivers. The fifth and sixth steps 614, 616 can combine to form a current medical pump status information display loop 618, which can continuously be performed at regular intervals within a programming loop for making sure the central (monitoring) computer 202, 302 has received the most current medical pump status information and values and for making sure that the most current medical pump status information and values are displayed on the caregiver (monitoring) computer or caregiving computer 240, 340.

Similar to the current patient condition information display loop 538 described in relation to FIG. 5, to obtain, display, and make decisions based on current patient condition information, in a seventh step 620, the central (monitoring) computer 202, 302 transmits a request to the medical pump 10, 210, 310/network bridge 230 to get or obtain monitored values. In one embodiment, the central (monitoring) computer 202, 302 transmits a request to obtain patient condition information and/or transmits a patient condition information request to the medical pump 10, 210, 310/network bridge 230 to obtain the current patient condition information for a patient. As mentioned, the patient condition information can include, but is not limited to, $EtCO_2$, $SpO_2$, respiratory rate, heart rate, and other patient condition information. Other patient condition information can include monitor alarms, alerts or similar information regarding the patient's condition. The medical pump 10, 210, 310/network bridge 230 receives the patient condition information request to obtain the current patient condition information for the patient, and in an eighth step 622, transmits the current patient condition information for the patient to the central (monitoring) computer 202, 302. The central (monitoring) computer 202, 302 receives the current patient condition information and can store the current patient condition information in a memory, such as the central memory of the central computer 202, 302. In one embodiment, the central (monitoring) computer 202, 302 will only store patient values for current patient condition information when a value has changed. Thus, previously obtained patient condition information values will remain in the central memory if such the current values received from the medical pump 310/network bridge 230 have not changed. In a ninth step 536, the central (monitoring) computer 202, 302 transmits the received/current patient condition information to the caregiver (monitoring) computer or caregiving computer 240, 340. As described, one example of where a caregiver (monitoring) computer or caregiving computer 240, 340 is used and located is at a nurses' station within a hospital. The caregiver (monitoring) computer or caregiving computer 240, 340 then displays the received/current patient condition information within an interface screen for viewing by one or more caregivers. In a tenth step 626, the central (monitoring) computer and software application therein uses the received current patient condition information and compares one or more of the patient condition information values to one or more predetermined patient condition threshold values, ranges and/or states in order to determine whether the patient is undergoing respiratory distress, or some other medical condition. For example, if a patient's $EtCO_2$ is greater than a predetermined threshold, then the central (monitoring) computer 202, 302 can be configured to conclude that the patient is experiencing respiratory distress. As another example, if a patient's $SpO_2$, respiratory rate and/or heart rate is less than predetermined thresholds, then the central (monitoring) computer 202, 302 can be configured to conclude that the patient is experiencing respiratory distress. The seventh, eighth, ninth, and tenth steps 620, 622, 624, 626 can combine to form a monitoring, displaying and detecting loop 628, which can continuously be performed at regular intervals within a programming loop for making sure the central (monitoring) computer 202, 302 has received the most current patient condition information values, for making sure that the most current patient condition information values are displayed on the caregiver (monitoring) computer or caregiving computer 240, 340, and in one embodiment, for detecting respiratory distress of a patient.

In an eleventh step 630, if the central (monitoring) computer 202, 302 detects that the patient being monitored is experiencing respiratory distress, then the central (monitoring) computer 202, 302 can be configured to transmit a pause infusion signal to the central (medication management) computer 202, 302 for pausing the medical pump 10, 210, 310 that is providing medication, such as analgesic to the patient for which the central (monitoring) computer 202, 302 determined that respiratory distress was occurring. The pause infusion signal can include the medical pump ID of the medical pump 10, 210, 310 providing medication to the patient and/or other identification information, such as for example patient ID, for use in determining which medical pump 10, 210, 310 should be paused. In a twelfth step 632, when the central (medication management) computer 202, 302 receives the pause infusion signal and transmits a further pause infusion signal to the medical pump 10, 210, 310 providing medication to the patient, to pause or shut down the medical pump 10, 210, 310. In a thirteenth step 634, the central (monitoring) computer 202, 302 can also be configured to transmit a page to a PDA 250, 350 device that the caregiver responsible for the patient is using and/or carrying. Likewise, the central computer 202, 302 can be configured to transmit the current patient condition information and/or current medical pump status information received by the central computer 202, 302 to the PDA 250, 350, and the PDA 250, 350 can be configured to receive and display the current patient condition information and/or the current medical pump status information within one or more interface screens on the PDA display.

Referring to FIG. 7, one embodiment of a patient condition/medical pump status information interface screen display 700 is shown, which concurrently depicts at least a subset of patient condition information and medical pump status information for one or more patients. Advantageously, this screen 700 is not limited to display on a pump or monitor in the patient's room. This interface screen can be displayed on the display of the caregiver computer or caregiving computer 240, 340 and/or the caregiver PDA 250, 350, and/or the pump 10, 210, 310 and/or any other computer within the system 200, 300. The patient condition/medical pump status information interface screen display 700 includes a patient window or more preferably a plurality of patient windows 702, 704, 706, 708. Each patient window includes a room number 710 that may also include a room portion or bed identifier, a patient name or other patient identifying information 712, a medication name 714 and concentration 716 for each medication being administered to the patient. In one embodiment, the patient window includes pump/channel status indicator fields 711 that indicate the current status of each drug administration and pump/container type icons 713 that give a visual indication of the type of pump, container type and container status. When the caregiver is viewing a display 700 that is remote from the patient's room, it is useful to know if the container is empty and the type of container to bring for continued or subsequent infusions. In one embodiment where a touch screen display 700 is utilized, the user can touch the infusion status field 711 of interest and the processor causes further details about the status of a particular infusion to be displayed, as illustrated in patient window 704. A rate 718, a volume 720 and a time 719 is displayed, along with an area 721 for indication of or messages relating to any pump alarms on the corresponding pump or pump channel. One or more navigational guide bars 723 can be provided to return to infusion summaries or view additional infusions. Another portion of the patient window 702, 704, 706, 708 is devoted to patient condition or monitor information and can include in one embodiment respective areas or fields for respiration rate (RR) 722, pulse or heart rate 725, $EtCO_2$ value 724, SpO2 value 726 and an event/alarm region 728. The room number 710 is the room number where the identified patient and medical pump 10, 210, 310 is located. The patient name 712 is the name of the patient located in the identified room and which is being provided a medication delivery with the medical pump 10, 210, 310. The medication name 714 is the name of the medication that is being delivered to the patient with the medical pump 10, 210, 310. The concentration 716 is concentration of the medication that is being delivered to the patient with the medical pump 10, 210, 310. The rate 718 is the rate that the medication is being delivered to the patient with the medical pump 10, 210, 310, such as an infusion rate. The volume 720 is the volume of medication that has already been infused to the patient with the medical pump 10, 210, 310, such as a volume of medication already infused. Optionally, the volume could be expressed as the volume remaining to be infused or VTBI. The respiration rate (RR) 722 is the most current respiration rate of the patient, as measured by the patient monitor 70, 220, 320. The $EtCO_2$ value 724 is the most current $EtCO_2$ of the patient's blood, as measured by the patient monitor 70, 220, 320. The $SpO_2$ value 726 is the most current $SpO_2$ of the patient's blood, as measured by the patient monitor 70, 220, 320. The event/alarm region 728 provides a space within each patient window 702, 704, 706, 708 for monitor events/alarms/alerts to be displayed, such as a "High ETCO2" alarm/alert for example. As shown in FIG. 7, the patient window 702 shows that the pump has been "paused." For example this may have occurred as a result of the medical pump 10, 210, 310 and/or the central computer 202, 302 determining that an earlier $EtCO_2$ value 724 of "65" is greater than a predetermined $EtCO_2$ limit value and that the patient might be experiencing respiratory distress. As a result, the medical pump 10, 210, 310 has been paused in view of the determined respiratory distress. The pump or monitor event/alarm/alert 721, 728 can be highlighted, such as in the color red or yellow. In addition, the patient condition value that is outside of the predetermined value or range, which is determined to create a potential respiratory distress situation, can also be highlighted or identified with a special font, color or display scheme, such as the $EtCO_2$ value 724 being highlighted in yellow or red.

Figure 8:
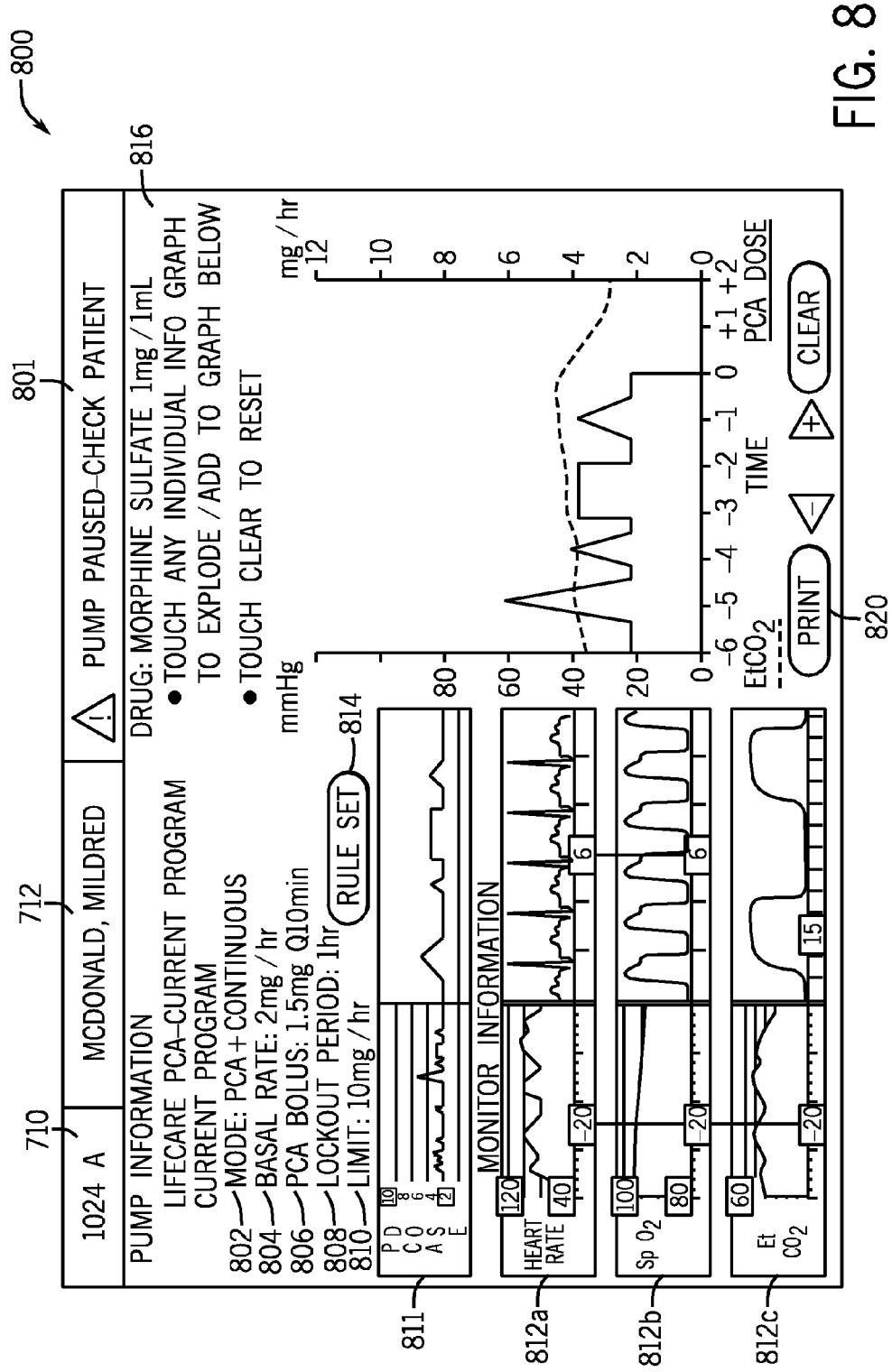
FIG. 8 is another embodiment of an interface screen display showing at least a subset of patient condition information and medical pump status information.

FIG. 8 is another embodiment of an interface screen display 800, and shows additional patient condition information and medical pump status information for one of the medication administrations from the first patient window 702. Specifically, the first patient window 702 of FIG. 7 regarding the patient Mildred McDonald is blown up and takes up most of the interface screen shown in FIG. 8. This interface screen can appear as a result of the caregiver selecting, touching, or "clicking on" the particular medication line of the patient window 702 in FIG. 7. Alternatively, this window may be accessed from or located on the pump 10, 210, 310 or patient monitor 70, 220, 320 in the patient's room or any other computer within the system. The top of the screen display 800 still shows the patient room number 710 and patient identifier or name 712. Prominently displayed at the top of the display 800 is a pump or monitor event/alarm/alert field 801 where messages, such as "Pump Paused—Check Patient" can be displayed. Again, a special set of symbols, font or color coding scheme can be used, as described above, to draw the caregiver or user's attention to the important information.

Pump information, including but not limited to delivery history on a short term and/or long term basis, current programming parameters, modes, settings, and infuser type or name can be displayed on one portion of the display 800. For example, medical pump status information is shown in this exemplary interface screen, including at least a delivery mode 802, basal rate 804, PCA bolus amount 806, lockout period 808 for the PCA bolus, lockout volume 810 for the PCA bolus. A history 811 of the medication administration can also be displayed above, below, side-by-side, or superimposed on top of monitor information such as one or more histories 812a, 812b and 812c of patient condition information collected by one or more monitors 70, 220, 320 within the system. Although many forms are possible such as tabular, etc., in the example shown, the histories are presented in graphical form and the history of medication administration 811 shows the PCA dose rate over time, the graph 812a shows the patient's heart rate in beats per minute, the graph 812b shows the percent of $SpO_2$ in the patient's blood, and the graph 812c shows the end tidal CO2 ($ETCO_2$) in mm-Hg. Each of the graphs 811, 812a, 812b, 812c can be presented with a plurality of different scales on the time axis. For example and not by way of limitation, one of the scales can be a relatively short time frame such as seconds or just a few minutes, while another of the scales can be a longer period of time such as several minutes, hours or days. The short time frame display allows the user to see current, real-time, near real-time, or recent status and visually analyze individual waveform characteristics, while the longer time frame display allows the user to understand trends, slopes, rates of change, derivatives or directional changes in the data, etc. Of course, data analysis can be performed by any of the computers within the system to advise the user of significant events, trends, changes, etc. based upon the data.

In the exemplary display of graphs 811, 812a, 812b, 812c of FIG. 8, both the long term and short term data is displayed concurrently. The long term data and short term data are displayed side-by-side and contiguous. The long term data is displayed on the left hand side and the short term data is displayed on the right hand side. The y-axis scales, legends, alarm/warning and stop limits can be pre-set by the manufacturer of the pump 10, 210, 310, monitor 70, 220, 320, or system. Alternatively, some or all of these items can be configured by the caregiver or other authorized person through a user customizable drug library or settings library that is downloadable to the pump, monitor or stored in memory of the system for use by the display 800. A "Rule Set" button 814 can be provided on the display 800 to recall from memory and display the rule set, rules, condition or limits used to generate alarms or other actions by the system, including but not limited to pausing delivery of medication from the medical pump 10, 210, 310, logging of events, notifying remote caregivers, etc. On another portion of the display 800 drug information 816 can be displayed, including but not limited to drug name, concentration, and units. A print button 820 can be provided on the display to print all or selected portions of the display 800 to a printer (not shown) for recordkeeping or caregiver review.

On yet another portion of the display 800 another graph 822 can be provided for analytical purposes. This analytical graph can comprise data from one or more of the graphs 811, 812a, 812b or 812c. The data to be displayed can be selected by touching the individual graph 811, 812a, 812b or 812c on the left. One or more graphs can be selected from the graphs 811, 812a, 812b or 812c on the left-hand portion of the display 800 and displayed concurrently in an overlaid or superimposed manner in the analytical graph 822 on the right-hand portion of the display 800. In the exemplary display 800 shown, the $ETCO_2$ data from graph 812c and the PCA Dose graph 811 have been selected for superimposed display on the analytical graph 822. The ETCO and PCA Dose plots can be displayed with different lines, symbols, or even colors. The latter is possible when the display 800 is presented on a pump with a color touch screen, such as the SYMBIQ infusion system sold by Hospira, Inc. of Lake Forest, Ill., USA. The graph 822 shows that an event occurred at time=0 a couple of minutes ago. For the purposes of this example and not for limitation, the event that occurred was that a rule involving a high $ETCO_2$ value was met, which caused the pump to pause delivery of medication. In this example, the continuous dose and the patient requested bolus or PCA demanded dose were both paused, but one skilled in the art will appreciate that only one of the continuous and PCA could be paused without affecting the other dose component. Advantageously the graph 822 displays how much time has elapsed since the event and has + and − navigation buttons 824, 826 respectively for reviewing the data at different points in time. By first touching a plot and then a navigation button 824 or 826, the plots can be manipulated separately with respect to time in order to explore whether there lead or lag relationships in the data. The patient requests for boluses are also marked on the PCA dose plot for easy reference. Touching or otherwise selecting a particular PCA bolus mark will provide a popup display (not shown) that notifies the clinician of the (clock) time at which the bolus request occurred and an indication of any limitation (given, limited, denied). Finally, a "Clear" button 828 is provided to allow the user to clear the contents of the graph 822. One skilled in the art will appreciate that clinicians are frequently presented with alarms on medical equipment, typically have a plethora of data that may or may not be relevant, but need to be able to decipher quickly what the problem is. For this reason, the processor may execute programming code stored in an associated memory to automatically display on the display 800 through the graphs 811, 812a, 0812b, etc, and/or graph 822 only the most relevant factors that led to the status displayed in the alert/alarm field 801. This may be a subset of the physiological or equipment conditions monitored.

Figure 9:
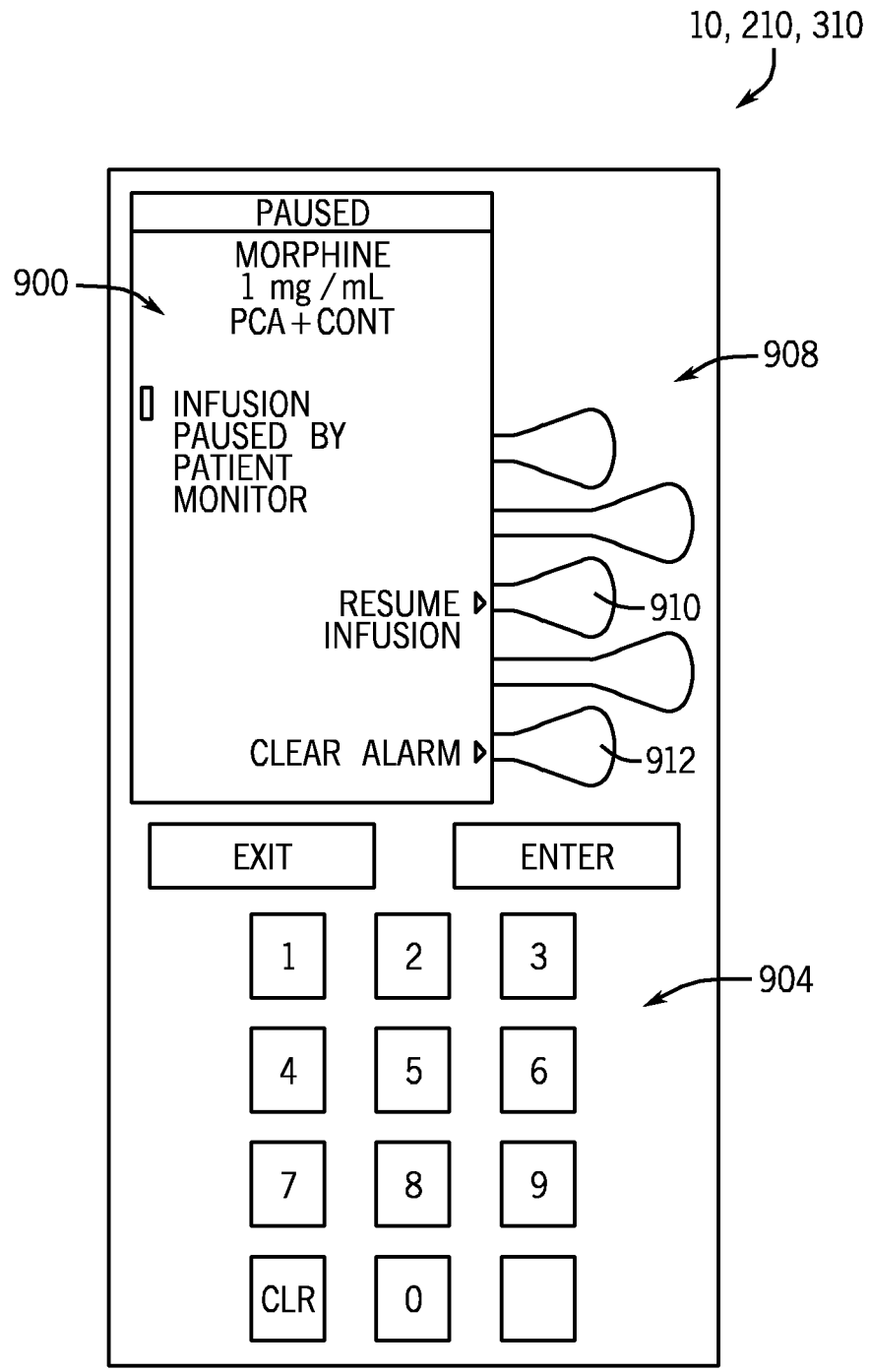
FIG. 9 is one embodiment of medial pump inputs/outputs, including an interface screen display showing at least a subset of patient condition information and medical pump status information.

The FIG. 9 is one embodiment of medical pump inputs/outputs, including an exemplary medical pump interface screen display 900 showing certain patient condition information and medical pump status information. The medical pump 10, 210, 310 has a numerical keypad 904, several soft keys 908, as well as "enter" and "exit" keys. In the embodiment shown, the soft keys 908 are programmed to include a "resume infusion" key 910 and a "clear alarm" key 912 for the interface screen 900 that appears in FIG. 9. The interface screen display 900 shown also depicts that the medical pump 10, 210, 310 has been paused, stating "Infusion Paused By Patient Monitor", with a "Paused" indicator highlighted at the top of the interface screen 900. In one embodiment, based on the current patient condition information received from the patient condition monitor 70, 220, 320, when monitor 70, 220, 320, central computer 202, 302, or medical pump 10, 210, 320 determines that the patient is experiencing respiratory distress and transmits a pause infusion signal to the medical pump 10, 210, 310, the medical pump 10, 210, 310 is paused and the "Infusion Paused By Patient Monitor" message can displayed on the interface screen display 900 of the medical pump 10, 210, 310, as shown in FIG. 9. Other messages and indicators can be used as well, including data shown in FIGS. 7 and 8.

The patient condition monitor 70, 220, 320 can have its own identification provided via barcode, RFID or in another manner to facilitate the establishment of a monitoring session or association with a particular patient, medical pump or other system component. One will appreciate from the description herein that the determination of patient condition based alarms and alerts can be done in any one of the computers or processors within the system or distributed among them without detracting from the invention. It should be emphasized that the above-described embodiments of the present invention are examples of implementations, and are merely set forth for a clear understanding of the principles of the invention. Many variations and modifications may be made to the above-described embodiment(s) of the invention without substantially departing from the principles of the invention. All such modifications are intended to be included herein within the scope of this disclosure and by the following claims.

What is claimed is:

1. A method for monitoring a patient, comprising:
   receiving patient condition information from a patient condition monitor at a central computer having a medication management application, wherein the patient condition information is continuously received and updated in response to the medication management application and central computer transmitting update request signals to the patient condition monitor, for forming a first information loop between the central computer and the patient condition monitor;
   receiving medication delivery status information from a medical pump by the medication management application within the central computer, wherein the medication delivery status information is continuously received and updated in response to the medication management application and central computer transmitting request signals to the medical pump, for forming a second information loop between the central computer and the medical pump;
   transmitting the patient condition information and the medication delivery status information to an interface screen from the medication management application and central computer, wherein the patient condition information comprises patient identification information and physiological condition data adapted to be displayed on the interface display in a graphical format, and wherein the medical pump information comprises at least one of an icon for giving a visual indication of a infusion pump type, an icon for giving a visual indication of a medication container type, and an icon for giving a visual indication of a medication container status, and wherein the patient condition information and the medical pump information is adapted to be displayed concurrently on the interface screen display.

2. The method of claim 1, wherein the patient condition information received from the patient condition monitor are in response to receiving patient condition signals at the patient condition monitor having a patient monitoring application, for monitoring at least one condition of the patient, wherein the patient condition signals represent patient condition information comprising at least one condition of the patient.

3. The method of claim 1, wherein the patient condition information is received at the medication management application and central computer from a medical pump having a medication delivery application, the patient condition information having been previously received at the medical pump from the patent monitoring application and patient condition monitor.

4. The method of claim 3, wherein the medication delivery application within the medical pump is adapted to track and store the medication delivery status information, wherein the medication delivery status information represents a status of medication delivery provided by the medical pump.

5. The method of claim 1, wherein the medication delivery status information is medical pump status information.

6. The method of claim 1, wherein the patient identification information is selected from the group: patient name, patient room number, patient bed number, and patient room portion.

7. The method of claim 1, wherein the physiological condition data displayed in a graphical format is selected from the group: EEG, ECG, temperature, blood pressure, Sp02, C02, Sa02, heart rate, pulse rate, cardiac output, respiration rate, blood glucose, blood gases and electrolytes.

8. The method of claim 1, wherein the central computer comprises a central memory and a central processor that is associated with medication management system through a communications network.

9. The method of claim 1, wherein the patient condition information and the medical pump information is received, transmitted, or requested through a manual action, an automated action, or a combination thereof.

10. The method of claim 9, wherein the automated action comprises transmitting or receiving a command or transmitting or receiving information to or from the central computer.

11. The method of claim 9, wherein the manual action comprises pressing a button or using a bar code or other type of scanner.

12. A method for monitoring a patient, comprising:
   receiving patient condition information from a patient condition monitor at a central computer having a medication management application, wherein the patient condition information is continuously received and updated in response to the medication management application and central computer transmitting update request signals to the patient condition monitor, for forming a first information loop between the central computer and the patient condition monitor;
   receiving medication delivery status information from a medical pump by the medication management application within the central computer, wherein the medication delivery status information is continuously received and updated in response to the medication management application and central computer transmitting request signals to the medical pump, for forming a second information loop between the central computer and the medical pump;
   transmitting the patient condition to an interface screen on the medical pump or caregiver computer from the medication management application and central computer, wherein the patient condition information is displayed on the interface screen in a graphic format; and selecting to view the medication delivery status information from the interface screen displaying the patient condition information in a graphic format;

receiving a selection to view the medication delivery status information in response to a selection made from the interface screen display displaying the patient condition information in graphic format.

13. The method of claim 12, wherein the medication delivery status information comprises rule sets, rules, conditions or limits used to generate alarms or pause delivery of medication from the medical pump.

* * * * *